United States Patent
Krauss et al.

(10) Patent No.: US 7,196,087 B2
(45) Date of Patent: Mar. 27, 2007

(54) QUINAZOLINONE AND BENZOXAZINONE DERIVATIVES AND USES THEREOF

(75) Inventors: Nancy Elisabeth Krauss, Mountain View, CA (US); Meng Sui, Union City, CA (US); Shu-Hai Zhao, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/035,506

(22) Filed: Jan. 14, 2005

(65) Prior Publication Data

US 2005/0165001 A1 Jul. 28, 2005

Related U.S. Application Data

(60) Provisional application No. 60/537,080, filed on Jan. 16, 2004.

(51) Int. Cl.
C07D 403/10 (2006.01)
C07D 403/14 (2006.01)
A61K 31/517 (2006.01)

(52) U.S. Cl. ............ 514/252.17; 544/286; 514/252.17; 514/212.02; 514/217.05; 540/543; 540/553; 540/599

(58) Field of Classification Search ............... 544/286; 514/266.22, 252.17, 212.02, 217.05; 540/553, 540/543, 599
See application file for complete search history.

(56) References Cited

U.S. PATENT DOCUMENTS

| 3,819,625 A | 6/1974 | Ott |
| 4,387,223 A | 6/1983 | Yamamoto et al. |
| 2003/0078255 A1 | 4/2003 | Pinto |

FOREIGN PATENT DOCUMENTS

| WO | WO 98/18781 A2 | 5/1998 |
| WO | WO 98/42688 A1 | 10/1998 |
| WO | WO 99/21840 A1 | 5/1999 |
| WO | WO 99/37643 A1 | 7/1999 |
| WO | WO 01/37837 A1 | 5/2001 |
| WO | WO 01/44228 A2 | 6/2001 |

OTHER PUBLICATIONS

Russell MG and Dias R. (Curr. Top. Med. Chem, Jun. 2002; 2(6):643-54).*

* cited by examiner

*Primary Examiner*—Kahsay Habte
(74) *Attorney, Agent, or Firm*—Robert C. Hall

(57) ABSTRACT

Compounds of the formula I:

and pharmaceutically acceptable salts thereof, wherein X is CH or N, Y is C or S, Z is $-(CR^aR^b)_r-$ or $-SO_2-$, A is $-NR^3-$ or $-O-$, $R^2$ is optionally substituted aryl or optionally substituted heteroaryl, n is 1 or 2, m is 1 when Y is C and m is 2 when Y is S, and p, q, r, $R^1$, $R^3$, $R^4$, $R^5$, $R^6$, $R^7$, $R^8$, $R^9$, $R^{10}$, $R^a$ and $R^b$ are as defined herein. The compounds are useful in the treatment of $5\text{-HT}_6$ and $5\text{-HT}_{2A}$ mediated diseases.

19 Claims, No Drawings

QUINAZOLINONE AND BENZOXAZINONE DERIVATIVES AND USES THEREOF

CROSS REFERENCE TO RELATED APPLICATIONS

This application claims benefit under 35 U.S.C. 119(e) of U.S. Provisional Application No. 60/537,080 filed Jan. 16, 2004, which is hereby incorporated by reference in its entirety

FIELD OF THE INVENTION

This invention relates to substituted quinazolinone compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403–14120, D. R. Sibley et al., Mol. Pharmacol., 1993, 43, 320–327, A. J. Sleight et al., Neurotransmission, 1995, 11, 1–5, and A. J. Sleight et al., Serotonin ID Research Alert, 1997, 2(3), 115–8.

While some 5-HT6 and 5-HT2A modulators have been disclosed, there continues to be a need for compounds that are useful for modulating the 5-HT6 receptor, the 5-HT2A receptor, or both.

SUMMARY

The invention provides compounds of the formula I:

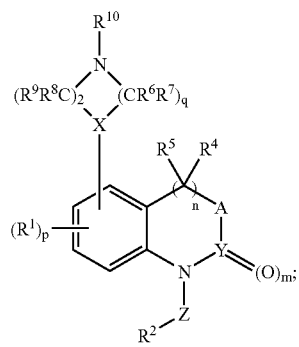

or a pharmaceutically acceptable salt, solvate or prodrug thereof, wherein:
Y is C or S;
m is 1 when Y is C and m is 2 when Y is S;
n is 1 or 2;
p is from 0 to 3;
q is from 1 to 3;
Z is —$(CR^aR^b)_r$— or —$SO_2$—, wherein r is from 0 to 2 and each of $R^a$ and $R^b$ is independently hydrogen or alkyl;
X is CH or N;
each $R^1$ independently is: halo; alkyl; haloalkyl; heteroalkyl; alkoxy; cyano; —$S(O)_s$—$R^c$; —C(=O)—$NR^cR^d$; —$SO_2$—$NR^cR^d$; —$N(R^c)$—C(=O)—$R^d$; or —C(=O)$R^c$; where s is from 0 to 2 and each of $R^c$ and $R^d$ is independently hydrogen or alkyl;
$R^2$ is optionally substituted aryl or optionally substituted heteroaryl; preferably $R^2$ is aryl, and more preferably optionally substituted phenyl;
A is —$NR^3$— or —O— wherein $R^3$ is: hydrogen; alkyl, acyl, amidoalkyl, hydroxyalkyl or alkoxyalkyl; preferably $R^3$ is hydrogen, alkyl or amidoalkyl;
each of $R^4$ and $R^5$ is independently hydrogen or alkyl, or one of $R^4$ and $R^5$ together with $R^3$ and the atoms therebetween may form a ring of 3 to 7 members that optionally includes a nitrogen or oxygen heteroatom; and
each of $R^6$, $R^7$, $R^8$, $R^9$ and $R^{10}$ is independently hydrogen or alkyl, or one of $R^6$ and $R^7$ together with $R^{10}$ and the atoms to which they are attached may form a ring of 3 to 7 members, or of $R^6$ and $R^7$ together with the atoms to which they are attached may form a ring of 3 to 7 members, or one of $R^6$ and $R^7$ together with one of $R^8$ and $R^9$ and the atoms to which they are attached may form a ring of 3 to 7 members.

The invention also provides methods for preparing the aforementioned compounds. The subject methods may comprise, in certain embodiments, reacting a compound of the formula:

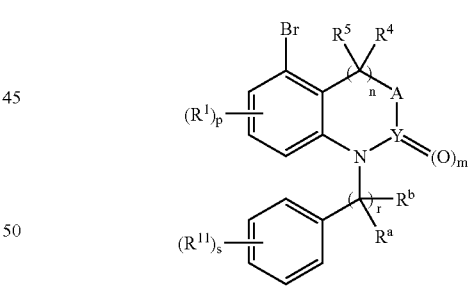

wherein Y, A, $R^1$, $R^4$, $R^5$, $R^{11}$, $R^a$, $R^b$, m, n, p, r and s are as defined herein,
with a heterocyclic amine of the formula:

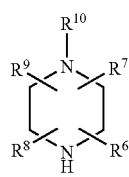

wherein $R^6$, $R^7$, $R^8$, $R^9$ and $R^{10}$ are as defined herein,
to yield the compound of the formula (IV):

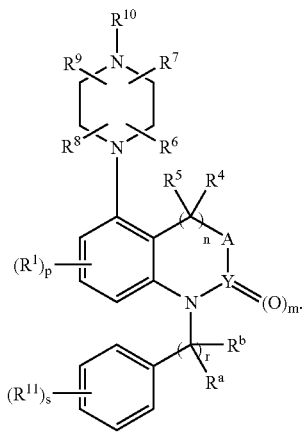

IV

The invention further provides compositions comprising, and methods for using the aforementioned compounds.

DETAILED DESCRIPTION OF THE INVENTION

The invention provides substituted quinolinone compounds, associated compositions, methods for use as therapeutic agents, and methods of preparation thereof. In specific embodiments the invention provides piperazinyl-substituted quinolinone compounds and associated pharmaceutical compositions, and methods for using the same in the treatment of central nervous system (CNS) diseases and gastrointestinal tract disorders.

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms (i.e. "$C_1$–$C_6$alkyl"). Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH=CH—), 2,2-dimethylethenylene, propenylene, 2-methylpropylene, butenylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylene" means a divalent aryl radical wherein aryl is as defined herein. "Arylene" includes, for example, ortho-, meta- and para- phenylene (1,2-phenylene, 1,3-phenylene and 1,4-phenylene respectively), which may be optionally substituted as defined herein.

"Arylalkyl" and "Aralkyl", which may be used interchangeably, mean a radical —$R^aR^b$ where $R^a$ is an alkylene group and $R^b$ is an aryl group as defined herein; e.g., benzyl, phenylethyl, 3-(3-chlorophenyl)-2-methylpentyl, and the like are examples of arylalkyl.

"Cycloalkyl" means a saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylmethyl, methylaminosulfonylmethyl, and the like.

"Heteroaryl" means a monocyclic or bicyclic monovalent radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyridinyl, pyridazyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylene" means a divalent heteroaryl radical wherein heteroaryl is as defined herein. "Heteroarylene" may be optionally substituted as defined herein. "Heteroarylene" includes, for example, indolylene, pyrimidinylene, and the like.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Optionally substituted", when used in association with "aryl", "arylene", phenyl", "phenylene", "heteroaryl", heteroarylene or "heterocyclyl", means an aryl, arylene, phenyl, phenylene, heteroaryl, heteroarylene, or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —$(CR'R")_n$—COOR (where n is an integer from 0 to 5, R' and R" are independently hydrogen or alkyl, and R is hydrogen, alkyl, cycloalkyl, cycloalkylalkyl, phenyl or phenylalkyl), or —$(CR'R")_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p1–92, Elesevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to choose a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity of the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. For convenience, the IUPAC numbering of the positions of representative quinolinone compounds described herein is shown by the formula:

In embodiments of the invention wherein X is a heteroatom, the benzoxazinone numbering system is used herein as shown by the formula:

Chemical structures shown herein were prepared using ISIS® version 2.2. Any open valency appearing on a carbon, oxygen or nitrogen atom in the structures herein indicates the presence of a hydrogen.

Compounds of the Invention

The invention provides compounds of the formula I:

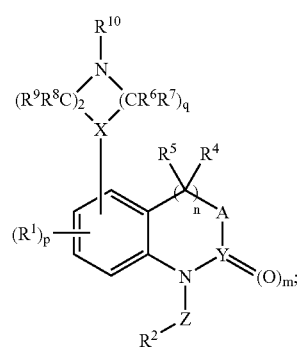

or a pharmaceutically acceptable salt, solvate or prodrug thereof,
wherein:

Y is C or S;

m is 1 when Y is C and m is 2 when Y is S;

n is 1 or 2; preferably n is 1;

p is from 0 to 3;

q is from 1 to 3; preferably q is 2

Z is —(CR$^a$R$^b$)$_r$— or —SO$_2$—, where r is from 0 to 2 and each of R$^a$ and R$^b$ is independently hydrogen or alkyl; preferably Z is —(CR$^a$R$^b$)$_r$—, r is 1, and R$^a$ and R$^b$ are hydrogen;

X is CH or N;

each R$^1$ independently is: halo; alkyl; haloalkyl; heteroalkyl; alkoxy; cyano; —S(O)$_s$—R$^c$; —C(=O)—NR$^c$R$^d$; —SO$_2$—NR$^c$R$^d$; —N(R$^c$)—C(=O)—R$^d$; or —C(=O)R$^c$; where s is from 0 to 2 and each of R$^c$ and R$^d$ is independently hydrogen or alkyl; preferably each R$^1$ is independently halo, alkyl or alkoxy;

R$^2$ is optionally substituted aryl or optionally substituted heteroaryl; preferably R$^2$ is aryl, and more preferably optionally substituted phenyl;

A is —NR$^3$— or —O— wherein R$^3$ is: hydrogen; alkyl, acyl, amidoalkyl, hydroxyalkyl or alkoxyalkyl; preferably R$^3$ is hydrogen, alkyl or amidoalkyl;

each of R$^4$ and R$^5$ is independently hydrogen or alkyl, or one of R$^4$ and R$^5$ together with R$^3$ and the atoms therebetween may form a ring of 3 to 7 members that optionally includes a nitrogen or oxygen heteroatom; and each of R$^6$, R$^7$, R$^8$, R$^9$ and R$^{10}$ is independently hydrogen or alkyl, or one of R$^6$ and R$^7$ together with R$^{10}$ and the atoms to which they are attached may form a ring of 3 to 7 members, or of R$^6$ and R$^7$ together with the atoms to which they are attached may form a ring of 3 to 7 members, or one of R$^6$ and R$^7$ together with one of R$^8$ and R$^9$ and the atoms to which they are attached may form a ring of 3 to 7 members.

The compounds of formula I may, in certain embodiments, be more specifically of the formula II:

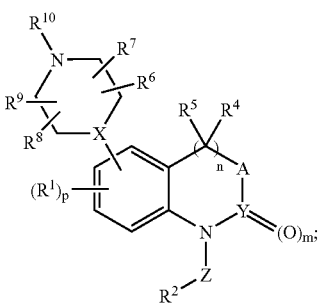

II wherein X, Y, Z, A, R$^1$, R$^2$, R$^4$, R$^5$, R$^6$, R$^7$, R$^8$, R$^9$, R$^{10}$, m, n, and p are as defined herein.

In many embodiments of formula I and formula II, n may be 1. In such embodiments Z may be —(CR$^a$R$^b$)$_r$—, and R$^a$ and R$^b$ in such embodiments are preferably hydrogen. In many embodiments of formula I and formula II, X is N and q is 2 and, in certain instances, r is 1.

In many embodiments of formula I and formula II, X is joined to the 5-position of the quinazolinone ring system.

In certain embodiments of formula I and formula II, R$^2$ is optionally substituted phenyl or optionally substituted naphthyl. Preferred R$^2$ in such embodiments include phenyl, 2-halophenyl, 3-halophenyl, 4-halophenyl, 2-cyanophenyl, 3-cyanophenyl, 4-cyanophenyl, 2-methoxyphenyl, 3-methoxyphenyl, 4-methoxyphenyl, 2,3-dihalophenyl, 2,4-dihalophenyl, 2,5-dihalophenyl, 2,6-dihalophenyl, 3,4-dihalophenyl, 3,5-dihalophenyl, 2-methylphenyl, 3-methylphenyl, and 2,2-dimethyl-2,3-dihydro-benzofuranyl, wherein each halo is independently fluoro or chloro. In other embodiments R$^2$ may be optionally substituted heteroaryl.

In certain embodiments of formula I and formula II, p is 0 or 1 and R$^1$ is halo, alky, haloalkyl, or alkoxy. Preferably R$^1$ is fluoro, chloro, methyl, ethyl, trifluormetyl, or methoxy.

In certain embodiments of formula I and formula II, A is —NR$^3$—. In such embodiments R$^4$ and R$^5$ are hydrogen. R$^3$ may hydrogen in such embodiments, or R$^3$ may be alkyl. In many embodiments R$^6$, R$^7$, R$^8$ and R$^9$ are hydrogen.

In certain embodiments of formula I and formula II, A is —O—.

In certain embodiments of formula I and formula II, Y is C and m is 1. In such embodiments R$^2$ may be optionally substituted phenyl or optionally substituted naphthyl. Preferred R$^2$ in such embodiments include phenyl, 2-halophenyl, 3-halophenyl, 4-halophenyl, 2-cyanophenyl, 3-cyanophenyl, 4-cyanophenyl, 2-methoxyphenyl, 3-methoxyphenyl, 4-methoxyphenyl, 2,3-dihalophenyl, 2,4-dihalophenyl, 2,5-dihalophenyl, 2,6-dihalophenyl, 3,4-dihalophenyl, 3,5-dihalophenyl, 2-methylphenyl, 3-methylphenyl, and 2,2-dimethyl-2,3-dihydro-benzofuranyl, wherein each halo is independently fluoro or chloro. In embodiments where Y is C and m is 1 p may be 0 or 1 while R$^1$ is halo, alkyl, haloalkyl or alkoxy. In such embodiments R$^4$ and R$^5$ may be hydrogen. In many embodiments where Y is C and m is 1, A is —NR$^3$—, and R$^3$ may be hydrogen, or R$^3$ may be alkyl. In such embodiments R$^6$, R$^7$, R$^8$ and R$^9$ are preferably hydrogen.

In certain embodiments of formula I and formula II, Y is S and m is 2. In such embodiments A is —O—, while in other embodiments A is —NR$^3$—. R$^2$ may, in such embodiments, be optionally substituted phenyl or optionally substituted naphthyl. Preferred R$^2$ include phenyl, 2-halophenyl, 3-halophenyl, 4-halophenyl, 2-cyanophenyl, 3-cyanophenyl, 4-cyanophenyl, 2-methoxyphenyl, 3-methoxyphenyl, 4-methoxyphenyl, 2,3-dihalophenyl, 2,4-dihalophenyl, 2,5-dihalophenyl, 2,6-dihalophenyl, 3,4-dihalophenyl, 3,5-dihalophenyl, 2-methylphenyl, 3-methylphenyl, or 2,2-dimethyl-2,3-dihydro-benzofuranyl, wherein each halo is independently fluoro or chloro.

In embodiments of formula I and formula II where Y is S, m is 2, and A is —NR$^3$— p is preferably 0 or 1, and R$^1$ is halo, methyl or methoxy. In such embodiments, R$^4$ and R$^5$ may be hydrogen. R$^6$, R$^7$, R$^8$ and R$^9$ may also be hydrogen. R$^3$ in some embodiments may be hydrogen, while in other embodiments R$^3$ may be alkyl.

In certain embodiments, the subject compounds may be more specifcally of the formula III:

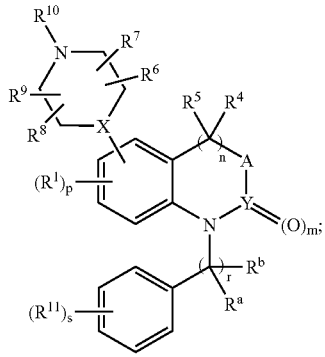

wherein:
s is from 0 to 4;
each $R^{11}$ independently is alkyl, alkoxy, halo, cyano or haloalkyl; and
X, Y, A, $R^1$, $R^2$, $R^4$, $R^5$, $R^6$, $R^7$, $R^8$, $R^9$, $R^{10}$, $R^a$, $R^b$, m, n, p and r are as defined herin.

In embodiments of formula III wherein X is N and is attached at the 5-position of the quinazolinone ring system, the subject compounds may be represented by the formula IV:

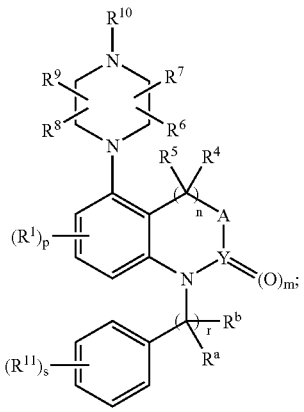

wherein Y, A, $R^1$, $R^2$, $R^4$, $R^5$, $R^6$, $R^7$, $R^8$, $R^9$, $R^{10}$, $R^{11}$, $R^a$, $R^b$, m, n, p, r and s are as defined herein.

In many embodiments of formula III and formula IV, n may be 1. In such embodiments $R^a$ and $R^b$ are preferably hydrogen. In many embodiments of formula III and formula IV, r is 1. In many embodiments of formula III and formula IV, $R^4$ and $R^5$ are hydrogen.

In certain embodiments of formula III and formula IV, s is 0, 1 or 2, and $R^{11}$ is halo, alkyl, haloalkyl or alkoxy. Preferably $R^{11}$ is fluoro, chloro, methyl, trifluoromethyl or methoxy.

In certain embodiments of formula III and formula IV, p is 0 or 1 and $R^1$ is halo, alkyl, haloalkyl or alkoxy. Preferably $R^1$ is fluoro, chloro, methyl, ethyl, trifluormethyl, or methoxy.

In certain embodiments of formula III and formula IV, A is —$NR^3$—. In such embodiments $R^4$ and $R^5$ are hydrogen. $R^3$ may hydrogen in such embodiments, or $R^3$ may be alkyl. In many embodiments $R^6$, $R^7$, $R^8$ and $R^9$ are hydrogen.

In certain embodiments of formula III and formula IV, A is —O—.

In certain embodiments of formula III and formula IV, Y is S and m is 2. In some such embodiments A is —O—, while in other embodiments A is —$NR^3$—. The variable s is 0, 1 or 2 in many such embodiments, and $R^{11}$ is halo, alkyl, haloalkyl or alkoxy. Preferably $R^{11}$ is fluoro, chloro, methyl, trifluorormethyl or methoxy.

In embodiments of formula III and formula IV where Y is S, m is 2, and A is —$NR^3$—, p is preferably 0 or 1, and $R^1$ is halo, methyl or methoxy. In such embodiments, $R^4$ and $R^5$ may be hydrogen. $R^6$, $R^7$, $R^8$ and $R^9$ may also be hydrogen. $R^3$ in some embodiments may be hydrogen, while in other embodiments $R^3$ may be alkyl. In such embodiments s is preferably 0, 1 or 2, and $R^{11}$ is halo, alkyl, haloalkyl or alkoxy. Preferably $R^{11}$ is fluoro, chloro, methyl, trifluoromethyl or methoxy.

In certain embodiments, the subject compounds may be more specifcally of the formula V:

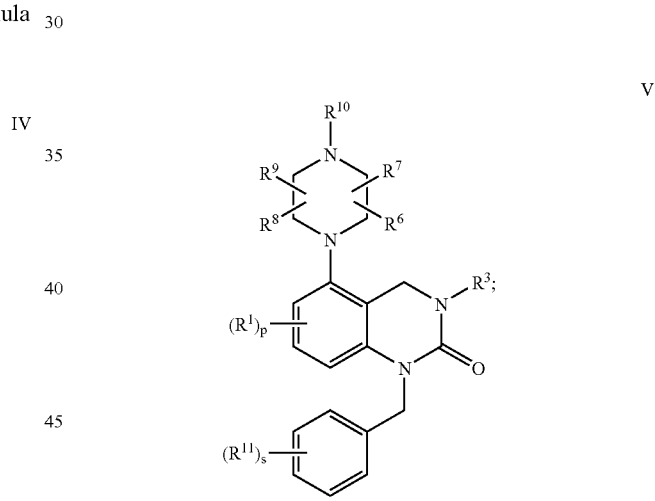

wherein $R^1$, $R^2$, $R^3$, $R^6$, $R^7$, $R^8$, $R^9$, $R^{10}$, $R^{11}$, p and s are as defined herein.

In certain embodiments of formula V, s is 0, 1 or 2, and $R^{11}$ is halo, alkyl, haloalkyl or alkoxy. Preferably $R^{11}$ is fluoro, chloro, methyl, trifluoromethyl or methoxy.

In certain embodiments of formula V, p is 0 or 1 and $R^1$ is halo, alkyl, haloalkyl or alkoxy. Preferably $R^1$ is fluoro, chloro, methyl, ethyl, trifluormethyl, or methoxy.

In certain embodiments of formula V, $R^4$ and $R^5$ are hydrogen. $R^3$ may hydrogen in such embodiments, or $R^3$ may be alkyl. In certain embodiments $R^3$ may be acetamidyl. In many embodiments $R^6$, $R^7$, $R^8$ and $R^9$ are hydrogen.

In certain embodiments, the subject compounds may be more specifically of the formula VI:

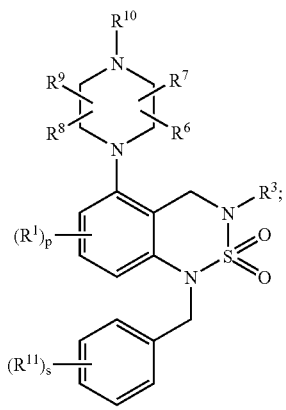

VI wherein $R^1$, $R^2$, $R^3$, $R^6$, $R^7$, $R^8$, $R^9$, $R^{10}$, $R^{11}$, p and s are as defined herein.

In certain embodiments of formula VI, s is 0, 1 or 2, and $R^{11}$ is halo, alkyl, haloalkyl or alkoxy. Preferably $R^{11}$ is fluoro, chloro, methyl, trifluoromethyl or methoxy.

In certain embodiments of formula VI, p is 0 or 1 and $R^1$ is halo, alkyl, haloalkyl or alkoxy. Preferably $R^1$ is fluoro, chloro, methyl, ethyl, trifluormethyl, or methoxy.

In certain embodiments of formula VI, $R^4$ and $R^5$ are hydrogen. In many embodiments $R^6$, $R^7$, $R^8$ and $R^9$ are hydrogen.

In embodiments of the invention where any of $R^1$, $R^2$, $R^3$, $R^4$, $R^5$, $R^6$, $R^7$, $R^8$, $R^9$, $R^{10}$, $R^a$, $R^b$, $R^c$ and $R^d$ are alkyl or an alkyl moiety, such alkyl is preferably are lower alkyl, i.e. $C_1$–$C_6$alkyl, and more preferably $C_1$–$C_4$alkyl. In embodiments where Y is S, A is preferably —$NR^3$—.

It should be understood that the scope of this invention encompasses not only the various isomers which may exist but also the various mixture of isomers which may be formed. Furthermore, the scope of the present invention also encompasses solvates and salts of compounds of formula I.

Representative compounds in accordance with the invention are shown in Table 1 together with melting point or mass spectrum M+H, and the experimental examples (described below) associated with each compound. Melting points shown are the the corresponding hydrochloride salts unless indicated otherwise.

TABLE 1

| # | Structure | Name (Autonom) | MP ° C. | Example |
|---|---|---|---|---|
| 1 | 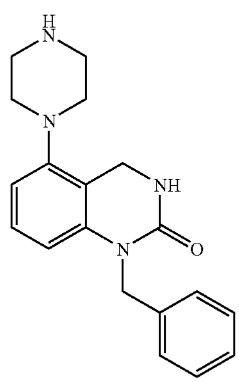 | 1-Benzyl-5-piperazin-1-yl-3,4-dihydro-1H-quinazolin-2-one | | 1 |
| 2 | 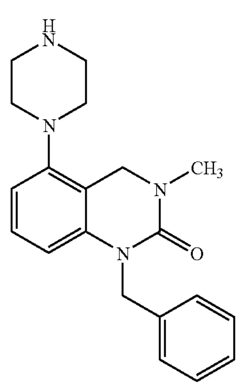 | 1-Benzyl-3-methyl-5-piperazin-1-yl-3,4-dihydro-1H-quinazolin-2-one | >300° C. | 3 |

TABLE 1-continued
| # | Structure | Name (Autonom) | MP ° C. | Example |
|---|---|---|---|---|
| 3 | 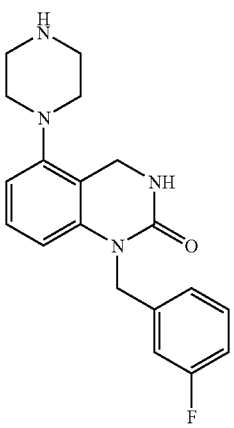 | 1-(3-Fluoro-benzyl)-5-piperazin-1-yl-3,4-dihydro-1H-quinazolin-2-one | >300° C. | 1 |
| 4 | 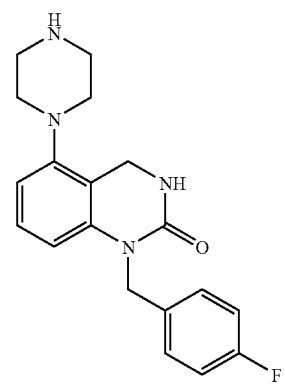 | 1-(4-Fluoro-benzyl)-5-piperazin-1-yl-3,4-dihydro-1H-quinazolin-2-one | >300° C. | 1 |
| 5 | 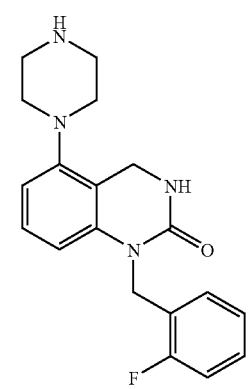 | 1-(2-Fluoro-benzyl)-5-piperazin-1-yl-3,4-dihydro-1H-quinazolin-2-one | | 1 |
| 6 | 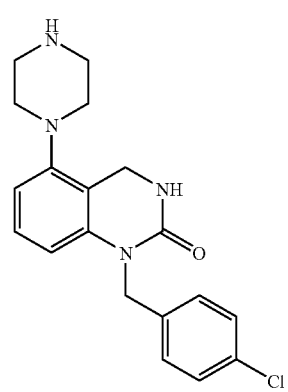 | 1-(4-Chloro-benzyl)-5-piperazin-1-yl-3,4-dihydro-1H-quinazolin-2-one | >300° C. | 1 |

TABLE 1-continued

| # | Structure | Name (Autonom) | MP ° C. | Example |
|---|-----------|----------------|---------|---------|
| 7 | 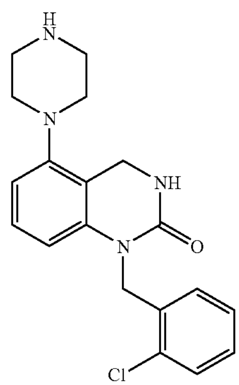 | 1-(2-Chloro-benzyl)-5-piperazin-1-yl-3,4-dihydro-1H-quinazolin-2-one | | 1 |
| 8 | 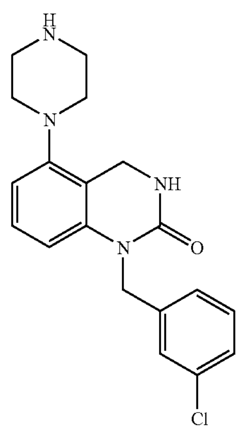 | 1-(3-Chloro-benzyl)-5-piperazin-1-yl-3,4-dihydro-1H-quinazolin-2-one | 281.0–282.8° C. | 1 |
| 9 | 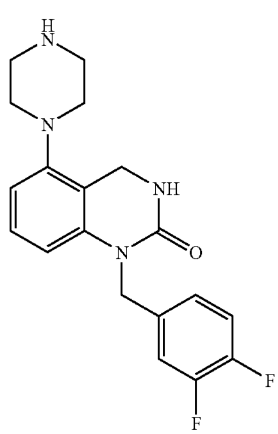 | 1-(3,4-Difluoro-benzyl)-5-piperazin-1-yl-3,4-dihydro-1H-quinazolin-2-one | >300° C. | 1 |

TABLE 1-continued

| # | Structure | Name (Autonom) | MP ° C. | Example |
|---|---|---|---|---|
| 10 | 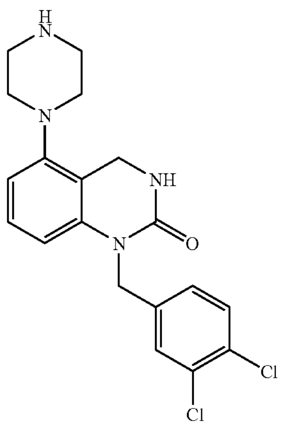 | 1-(3,4-Dichloro-benzyl)-5-piperazin-1-yl-3,4-dihydro-1H-quinazolin-2-one | >300° C. | 1 |
| 11 | 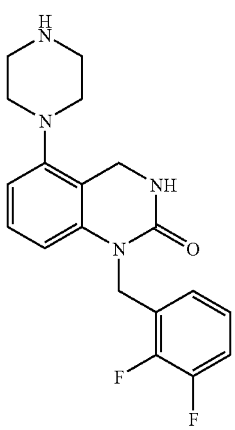 | 1-(2,3-Difluoro-benzyl)-5-piperazin-1-yl-3,4-dihydro-1H-quinazolin-2-one | >300° C. | 1 |
| 12 | 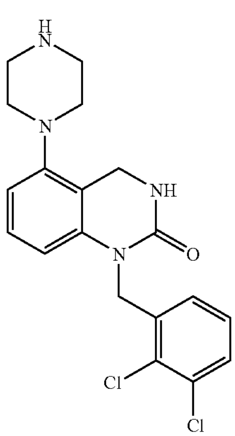 | 1-(2,3-Dichloro-benzyl)-5-piperazin-1-yl-3,4-dihydro-1H-quinazolin-2-one | 290.3–300° C. | 1 |

TABLE 1-continued

| # | Structure | Name (Autonom) | MP ° C. | Example |
|---|---|---|---|---|
| 13 | 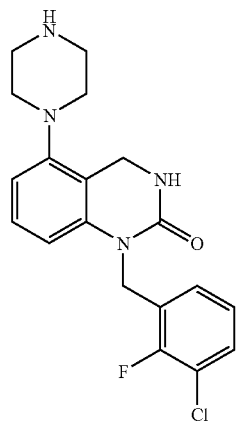 | 1-(3-Chloro-2-fluoro-benzyl)-5-piperazin-1-yl-3,4-dihydro-1H-quinazolin-2-one | 292.4–298.8° C. | 1 |
| 14 | 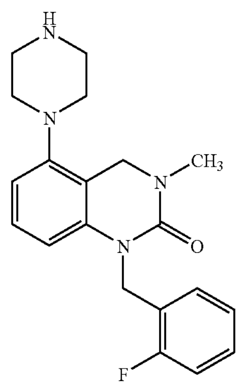 | 1-(2-Fluoro-benzyl)-3-methyl-5-piperazin-1-yl-3,4-dihydro-1H-quinazolin-2-one | >300° C. | 3 |
| 15 | 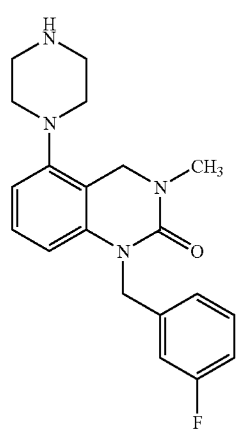 | 1-(3-Fluoro-benzyl)-3-methyl-5-piperazin-1-yl-3,4-dihydro-1H-quinazolin-2-one | | 3 |

TABLE 1-continued

| # | Structure | Name (Autonom) | MP ° C. | Example |
|---|---|---|---|---|
| 16 | 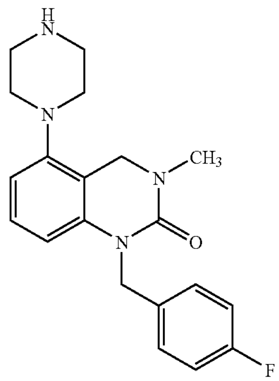 | 1-(4-Fluoro-benzyl)-3-methyl-5-piperazin-1-yl-3,4-dihydro-1H-quinazolin-2-one | | 3 |
| 17 | 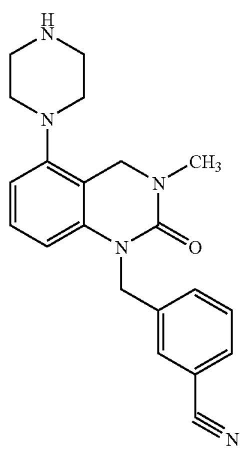 | 3-(3-Methyl-2-oxo-5-piperazin-1-yl-3,4-dihydro-2H-quinazolin-1-ylmethyl)benzonitrile | | 3 |
| 18 | 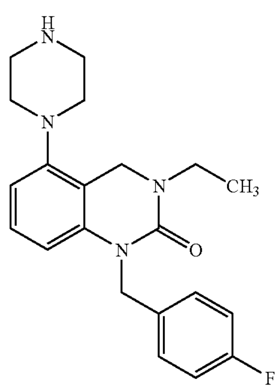 | 3-Ethyl-1-(4-fluoro-benzyl)-5-piperazin-1-yl-3,4-dihydro-1H-quinazolin-2-one | | 3 |
| 19 | 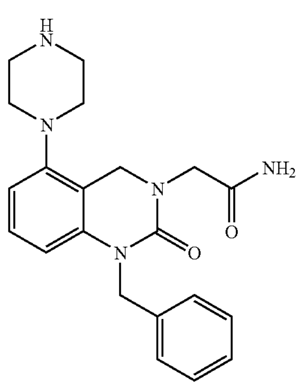 | 2-(1-Benzyl-2-oxo-5-piperazin-1-yl-1,4-dihydro-2H-quinazolin-3-yl)-acetamide | | 3 |

TABLE 1-continued

| # | Structure | Name (Autonom) | MP ° C. | Example |
|---|---|---|---|---|
| 20 | 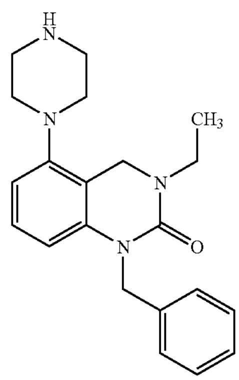 | 1-Benzyl-3-ethyl-5-piperazin-1-yl-3,4-dihydro-1H-quinazolin-2-one | | 3 |
| 21 | 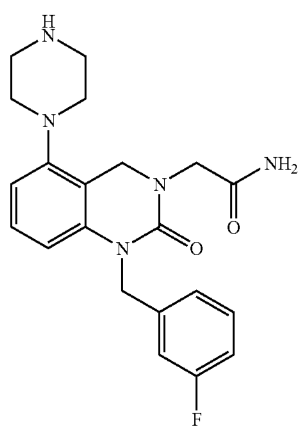 | 2-[1-(3-Fluoro-benzyl)-2-oxo-5-piperazin-1-yl-1,4-dihydro-2H-quinazolin-3-yl]-acetamide | | 3 |
| 22 | 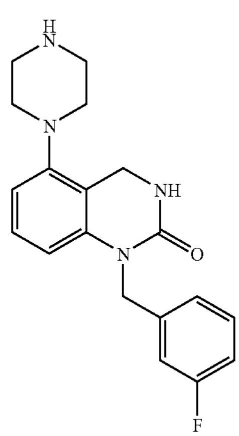 | 1-(3-Fluoro-benzyl)-5-piperazin-1-yl-3,4-dihydro-1H-quinazolin-2-one | | 1 |

TABLE 1-continued

| # | Structure | Name (Autonom) | MP ° C. | Example |
|---|---|---|---|---|
| 23 | 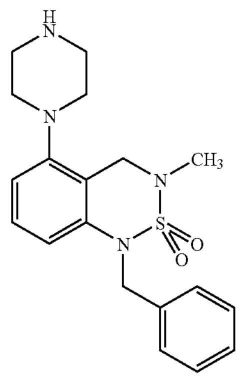 | 1-Benzyl-3-methyl-5-piperazin-1-yl-3,4-dihydro-1H-benzo[1,2,6]thiadiazine 2,2-dioxide | 250.0–250.4° C. | 4 |
| 24 | 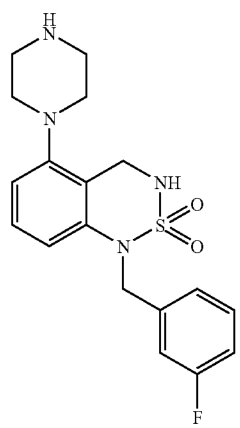 | 1-(3-Fluoro-benzyl)-5-piperazin-1-yl-3,4-dihydro-1H-benzo[1,2,6]thiadiazine 2,2-dioxide | 285.1–288.3° C. | 2 |
| 25 | 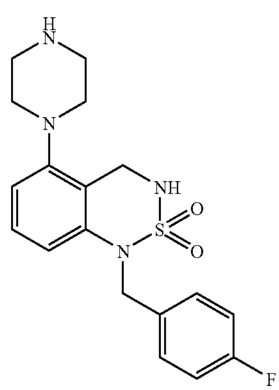 | 1-(4-Fluoro-benzyl)-5-piperazin-1-yl-3,4-dihydro-1H-benzo[1,2,6]thiadiazine 2,2-dioxide | 253.6–254.7° C. | 2 |
| 26 | 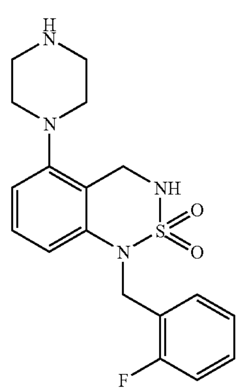 | 1-(2-Fluoro-benzyl)-5-piperazin-1-yl-3,4-dihydro-1H-benzo[1,2,6]thiadiazine 2,2-dioxide | >300° C. | 2 |

TABLE 1-continued

| # | Structure | Name (Autonom) | MP ° C. | Example |
|---|---|---|---|---|
| 27 | 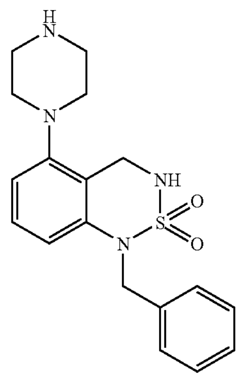 | 1-Benzyl-5-piperazin-1-yl-3,4-dihydro-1H-benzo[1,2,6]thiadiazine 2,2-dioxide | | 2 |
| 28 | 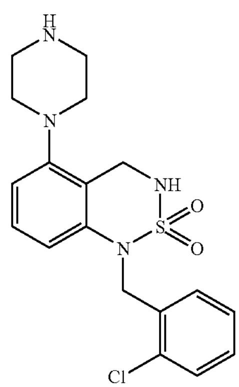 | 1-(2-Chloro-benzyl)-5-piperazin-1-yl-3,4-dihydro-1H-benzo[1,2,6]thiadiazine 2,2-dioxide | >300° C. | 2 |
| 29 | 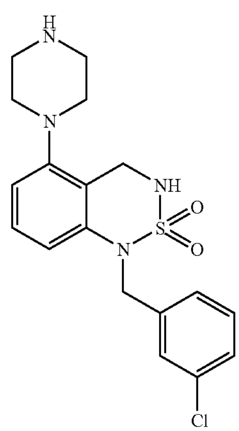 | | 264.7–265.5° C. | 2 |

TABLE 1-continued

| # | Structure | Name (Autonom) | MP ° C. | Example |
|---|---|---|---|---|
| 30 | 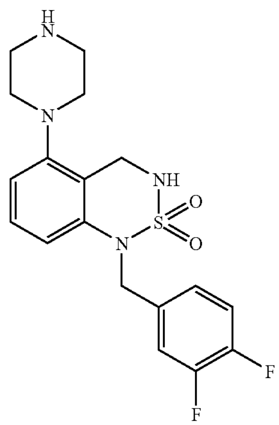 | 1-(3-Chloro-benzyl)-5-piperazin-1-yl-3,4-dihydro-1H-benzo[1,2,6]thiadiazine 2,2-dioxide | 278.2–286.4° C. | 2 |
| 31 | 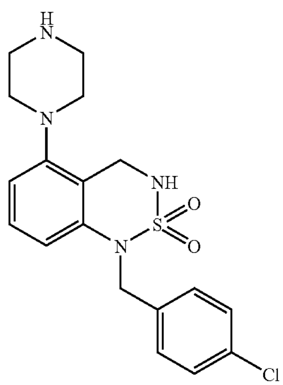 | 1-(4-Chloro-benzyl)-5-piperazin-1-yl-3,4-dihydro-1H-benzo[1,2,6]thiadiazine 2,2-dioxide | >300° C. | 2 |
| 32 | 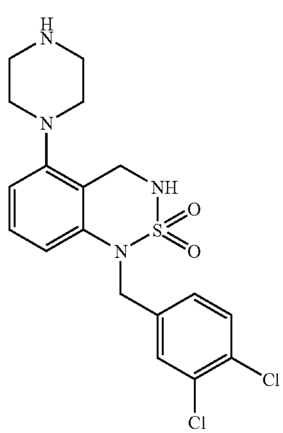 | 1-(3,4-Dichloro-benzyl)-5-piperazin-1-yl-3,4-dihydro-1H-benzo[1,2,6]thiadiazine 2,2-dioxide | >300° C. | 2 |

TABLE 1-continued

| # | Structure | Name (Autonom) | MP ° C. | Example |
|---|---|---|---|---|
| 33 | 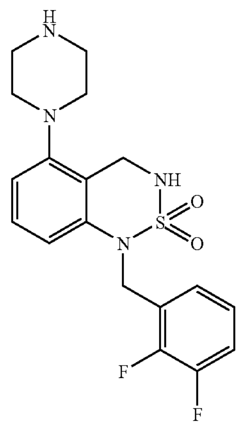 | 1-(2,3-Difluoro-benzyl)-5-piperazin-1-yl-3,4-dihydro-1H-benzo[1,2,6]thiadiazine 2,2-dioxide | | 2 |
| 34 | 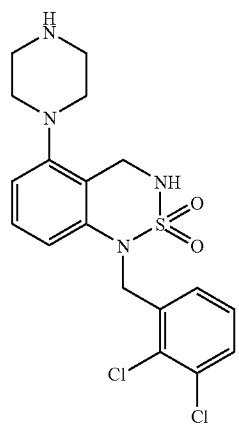 | 1-(2,3-Dichloro-benzyl)-5-piperazin-1-yl-3,4-dihydro-1H-benzo[1,2,6]thiadiazine 2,2-dioxide | 263.2–265.9° C. | 2 |
| 35 | 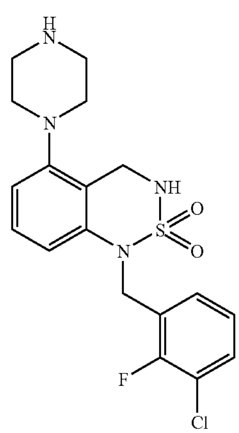 | 1-(3-Chloro-2-fluoro-benzyl)-5-piperazin-1-yl-3,4-dihydro-1H-benzo[1,2,6]thiadiazine 2,2-dioxide | 261.8–262.2° C. | 2 |

TABLE 1-continued

| # | Structure | Name (Autonom) | MP ° C. | Example |
|---|---|---|---|---|
| 36 | 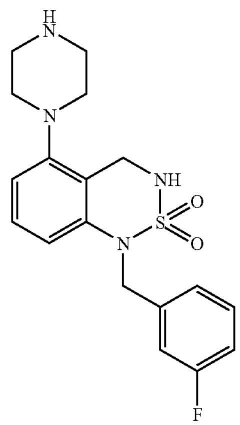 | 1-(3-Fluoro-benzyl)-5-piperazin-1-yl-3,4-dihydro-1H-benzo[1,2,6]thiadiazine 2,2-dioxide | | 2 |
| 37 | 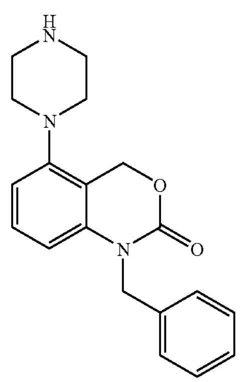 | 1-Benzyl-5-piperazin-1-yl-1,4-dihydro-benzo[d][1,3]oxazin-2-one | | 5 |
| 38 | 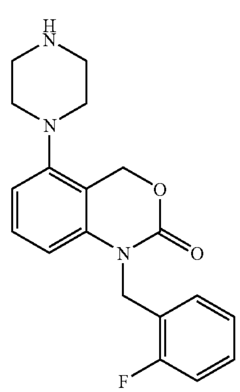 | 1-(2-Fluoro-benzyl)-5-piperazin-1-yl-1,4-dihydro-benzo[d][1,3]oxazin-2-one | | 5 |

TABLE 1-continued

| # | Structure | Name (Autonom) | MP ° C. | Example |
|---|---|---|---|---|
| 39 | 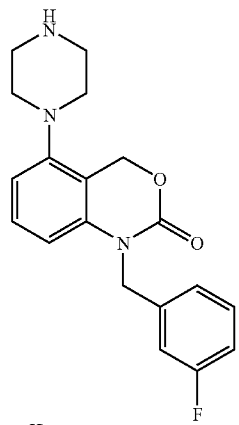 | 1-(3-Fluoro-benzyl)-5-piperazin-1-yl-1,4-dihydro-benzo[d][1,3]oxazin-2-one | | 5 |
| 40 | 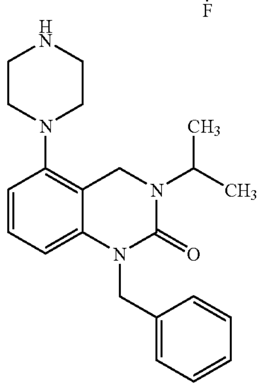 | 1-Benzyl-3-isopropyl-5-piperazin-1-yl-3,4-dihydro-1H-quinazolin-2-one | | 3 |
| 41 | 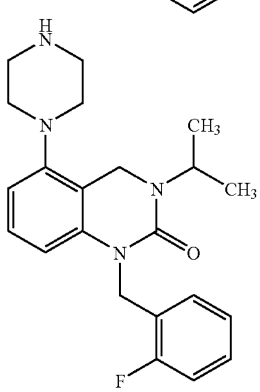 | 1-(2-Fluoro-benzyl)-3-isopropyl-5-piperazin-1-yl-3,4-dihydro-1H-quinazolin-2-one | | 3 |
| 42 | 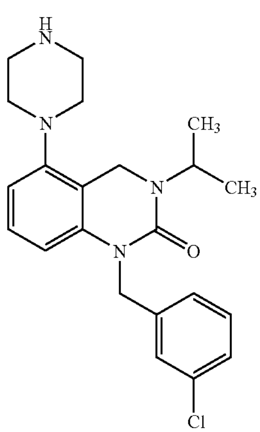 | 1-(3-Chloro-benzyl)-3-isopropyl-5-piperazin-1-yl-3,4-dihydro-1H-quinazolin-2-one | | 3 |

TABLE 1-continued

| # | Structure | Name (Autonom) | MP ° C. | Example |
|---|---|---|---|---|
| 43 | 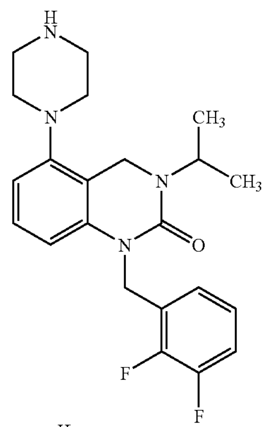 | 1-(2,3-Difluoro-benzyl)-3-isopropyl-5-piperazin-1-yl-3,4-dihydro-1H-quinazolin-2-one | | 3 |
| 44 | 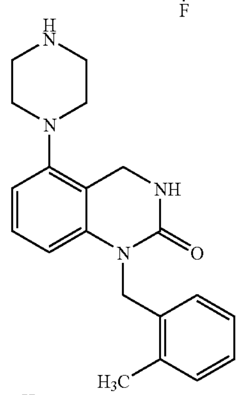 | 1-(2-Methyl-benzyl)-5-piperazin-1-yl-3,4-dihydro-1H-quinazolin-2-one | | 1 |
| 45 | 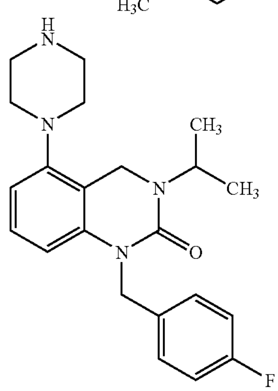 | 1-(4-Fluoro-benzyl)-3-isopropyl-5-piperazin-1-yl-3,4-dihydro-1H-quinazolin-2-one | | 3 |
| 46 | 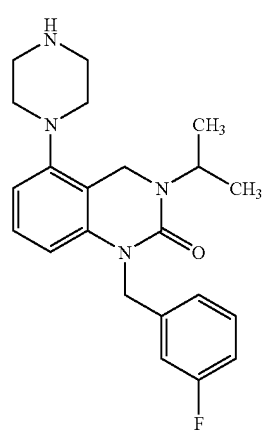 | 1-(3-Fluoro-benzyl)-3-isopropyl-5-piperazin-1-yl-3,4-dihydro-1H-quinazolin-2-one | | 3 |

TABLE 1-continued
| # | Structure | Name (Autonom) | MP ° C. | Example |
|---|---|---|---|---|
| 47 | 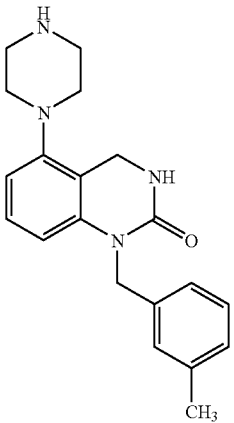 | 1-(2-Methyl-benzyl)-5-piperazin-1-yl-3,4-dihydro-1H-quinazolin-2-one | | 1 |
| 48 | 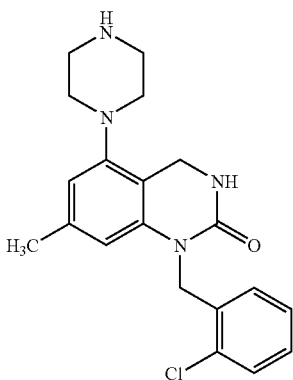 | 1-(2-Chloro-benzyl)-7-methyl-5-piperazin-1-yl-3,4-dihydro-1H-quinazolin-2-one | | 1 |
| 49 | 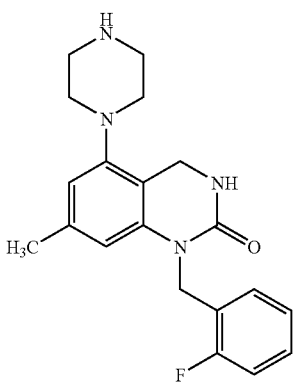 | 1-(2-Fluoro-benzyl)-7-methyl-5-piperazin-1-yl-3,4-dihydro-1H-quinazolin-2-one | | 1 |
| 50 | 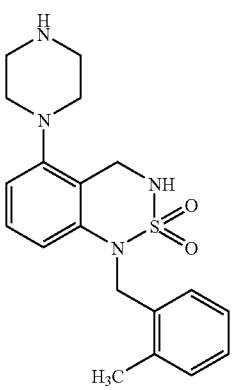 | 1-(2-Methyl-benzyl)-5-piperazin-1-yl-3,4-dihydro-1H-benzo[1,2,6]thiadiazine 2,2-dioxide | | 2 |

TABLE 1-continued

| # | Structure | Name (Autonom) | MP °C. | Example |
|---|---|---|---|---|
| 51 | 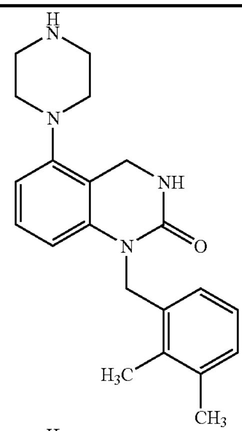 | 1-(2,3-Dimethyl-benzyl)-5-piperazin-1-yl-3,4-dihydro-1H-quinazolin-2-one | | 1 |
| 52 | 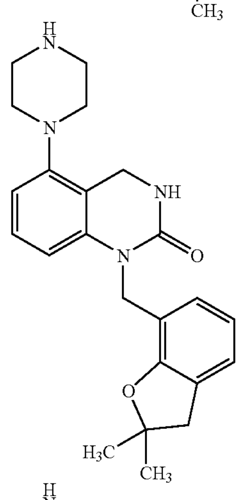 | 1-(2,2-Dimethyl-2,3-dihydro-benzofuran-7-ylmethyl)-5-piperazin-1-yl-3,4-dihydro-1H-quinazolin-2-one | | 1 |
| 53 | 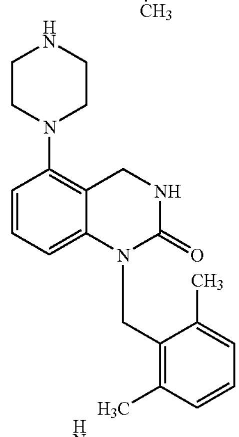 | 1-(2,6-Dimethyl-benzyl)-5-piperazin-1-yl-3,4-dihydro-1H-quinazolin-2-one | | 1 |
| 54 | 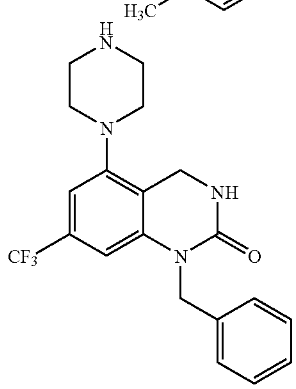 | 1-Benzyl-5-piperazin-1-yl-7-trifluoromethyl-3,4-dihydro-1H-quinazolin-2-one | | 1 |

TABLE 1-continued

| # | Structure | Name (Autonom) | MP ° C. | Example |
|---|---|---|---|---|
| 55 | 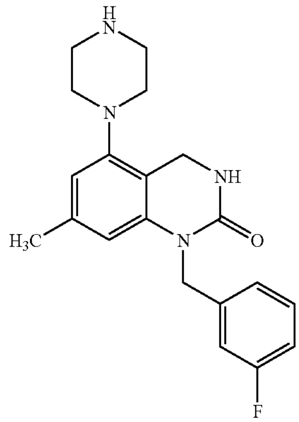 | 1-(3-Fluoro-benzyl)-7-methyl-5-piperazin-1-yl-3,4-dihydro-1H-quinazolin-2-one | | 1 |
| 56 | 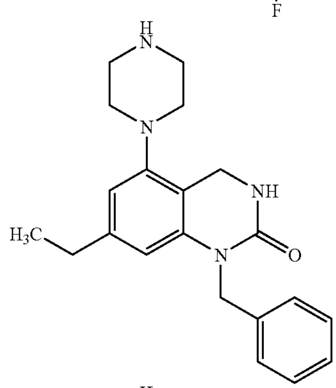 | 1-Benzyl-7-ethyl-5-piperazin-1-yl-3,4-dihydro-1H-quinazolin-2-one | | 1 |
| 57 | 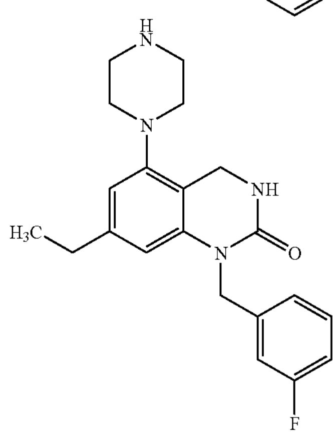 | 7-Ethyl-1-(3-fluoro-benzyl)-5-piperazin-1-yl-3,4-dihydro-1H-quinazolin-2-one | | 1 |
| 58 | 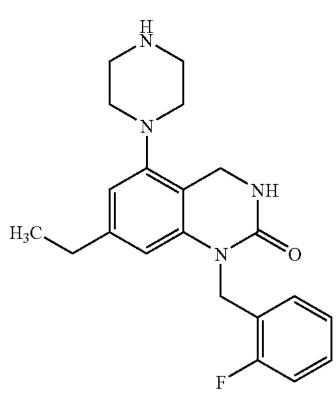 | 7-Ethyl-1-(2-fluoro-benzyl)-5-piperazin-1-yl-3,4-dihydro-1H-quinazolin-2-one | | 1 |

TABLE 1-continued

| # | Structure | Name (Autonom) | MP ° C. | Example |
|---|---|---|---|---|
| 59 | 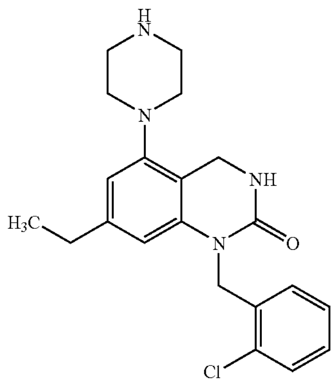 | 1-(2-Chloro-benzyl)-7-ethyl-5-piperazin-1-yl-3,4-dihydro-1H-quinazolin-2-one | | 1 |
| 60 | 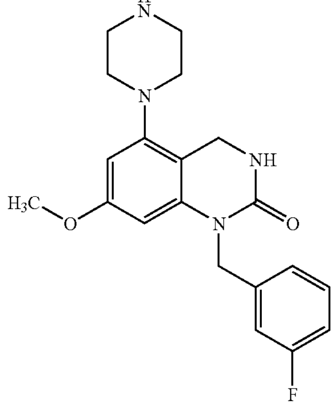 | 1-(3-Fluoro-benzyl)-7-methoxy-5-piperazin-1-yl-3,4-dihydro-1H-quinazolin-2-one | | 7 |
| 61 | 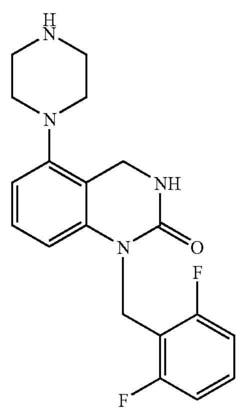 | 1-(2,6-Difluoro-benzyl)-5-piperazin-1-yl-3,4-dihydro-1H-quinazolin-2-one | | 1 |
| 62 | 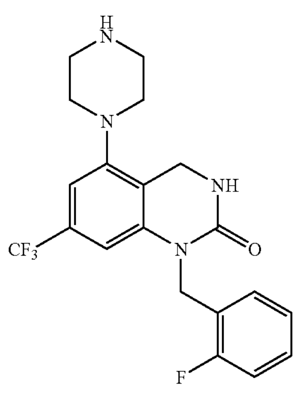 | 1-(2-Fluoro-benzyl)-5-piperazin-1-yl-7-trifluoromethyl-3,4-dihydro-1H-quinazolin-2-one | | 1 |

TABLE 1-continued

| # | Structure | Name (Autonom) | MP ° C. | Example |
|---|---|---|---|---|
| 63 | 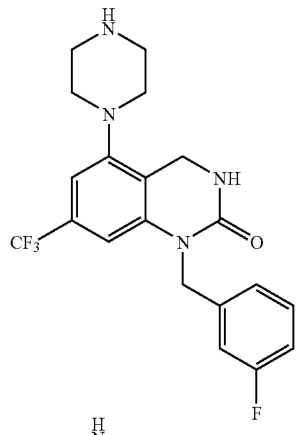 | 1-(3-Fluoro-benzyl)-5-piperazin-1-yl-7-trifluoromethyl-3,4-dihydro-1H-quinazolin-2-one | | 1 |
| 64 | 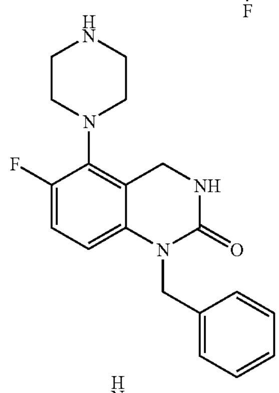 | 1-Benzyl-6-fluoro-5-piperazin-1-yl-3,4-dihydro-1H-quinazolin-2-one | 285.6–290.0° C. | 6 |
| 65 | 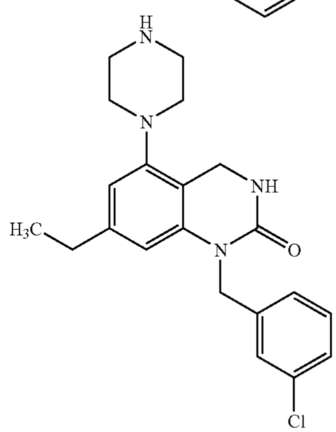 | 1-(3-Chloro-benzyl)-7-ethyl-5-piperazin-1-yl-3,4-dihydro-1H-quinazolin-2-one | | 1 |
| 66 | 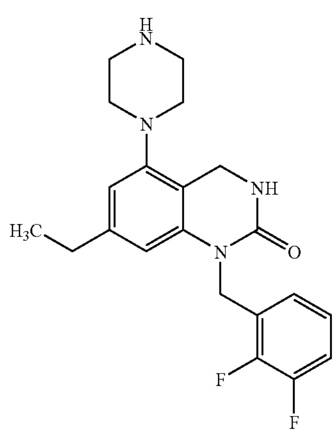 | 1-(2,3-Difluoro-benzyl)-7-ethyl-5-piperazin-1-yl-3,4-dihydro-1H-quinazolin-2-one | | 1 |

TABLE 1-continued

| # | Structure | Name (Autonom) | MP ° C. | Example |
|---|---|---|---|---|
| 67 | 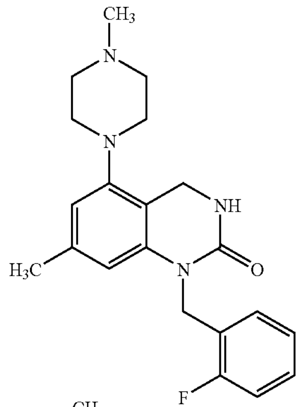 | 1-(2-Fluoro-benzyl)-7-methyl-5-(4-methyl-piperazin-1-yl)-3,4-dihydro-1H-quinazolin-2-one | | 1 |
| 68 | 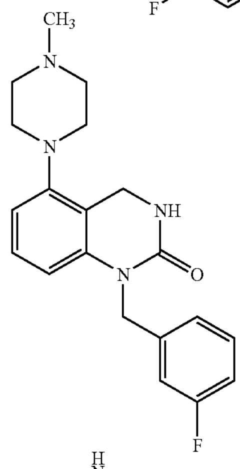 | 1-(3-Fluoro-benzyl)-5-(4-methyl-piperazin-1-yl)-3,4-dihydro-1H-quinazolin-2-one | | 1 |
| 69 | 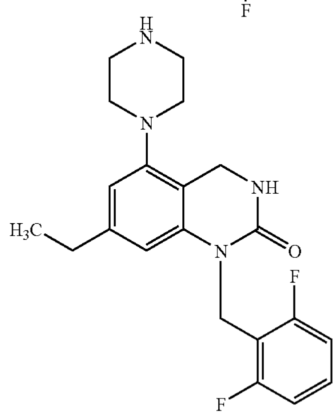 | 1-(2,6-Difluoro-benzyl)-7-ethyl-5-piperazin-1-yl-3,4-dihydro-1H-quinazolin-2-one | | 1 |
| 70 | 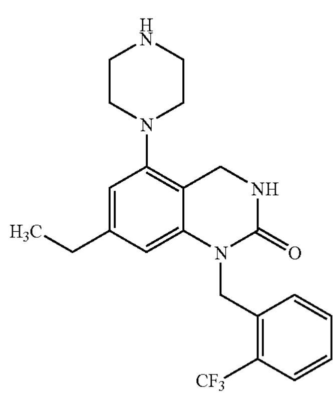 | 7-Ethyl-5-piperazin-1-yl-1-(2-trifluoromethyl-benzyl)-3,4-dihydro-1H-quinazolin-2-one | | 1 |

TABLE 1-continued

| # | Structure | Name (Autonom) | MP ° C. | Example |
|---|---|---|---|---|
| 71 | 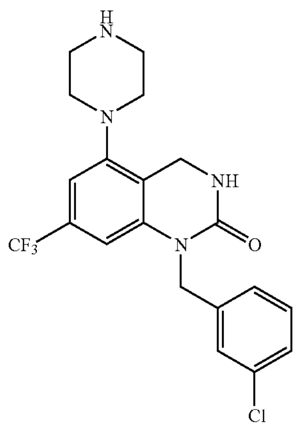 | 1-(3-Chloro-benzyl)-5-piperazin-1-yl-7-trifluoromethyl-3,4-dihydro-1H-quinazolin-2-one | | 1 |

Another aspect of the invention provides a composition comprising a therapeutically effective amount of at least one compound of formula (I) and a pharmaceutically acceptable carrier.

Yet another aspect of the invention provides a method for treating a central nervous system (CNS) disease state in a subject comprising administering to the subject a therapeutically effective amount of a compound of formula I. The disease state may comprise, for example, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a compound of formula (I).

Another aspect of the present invention provides a method for producing a compound of formula (I).

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein p, q, $R^1$, $R^2$, $R^6$, $R^7$, $R^8$, $R^9$, and $R^{10}$ are as defined herein. Numerous synthetic routes to quinazolinones and corresponding sulfonamides are known and may be used in preparation of the subject compounds, and the procedure of Scheme A is only exemplary. Specific examples of the procedure of Scheme A are provided in the following Experimental section.

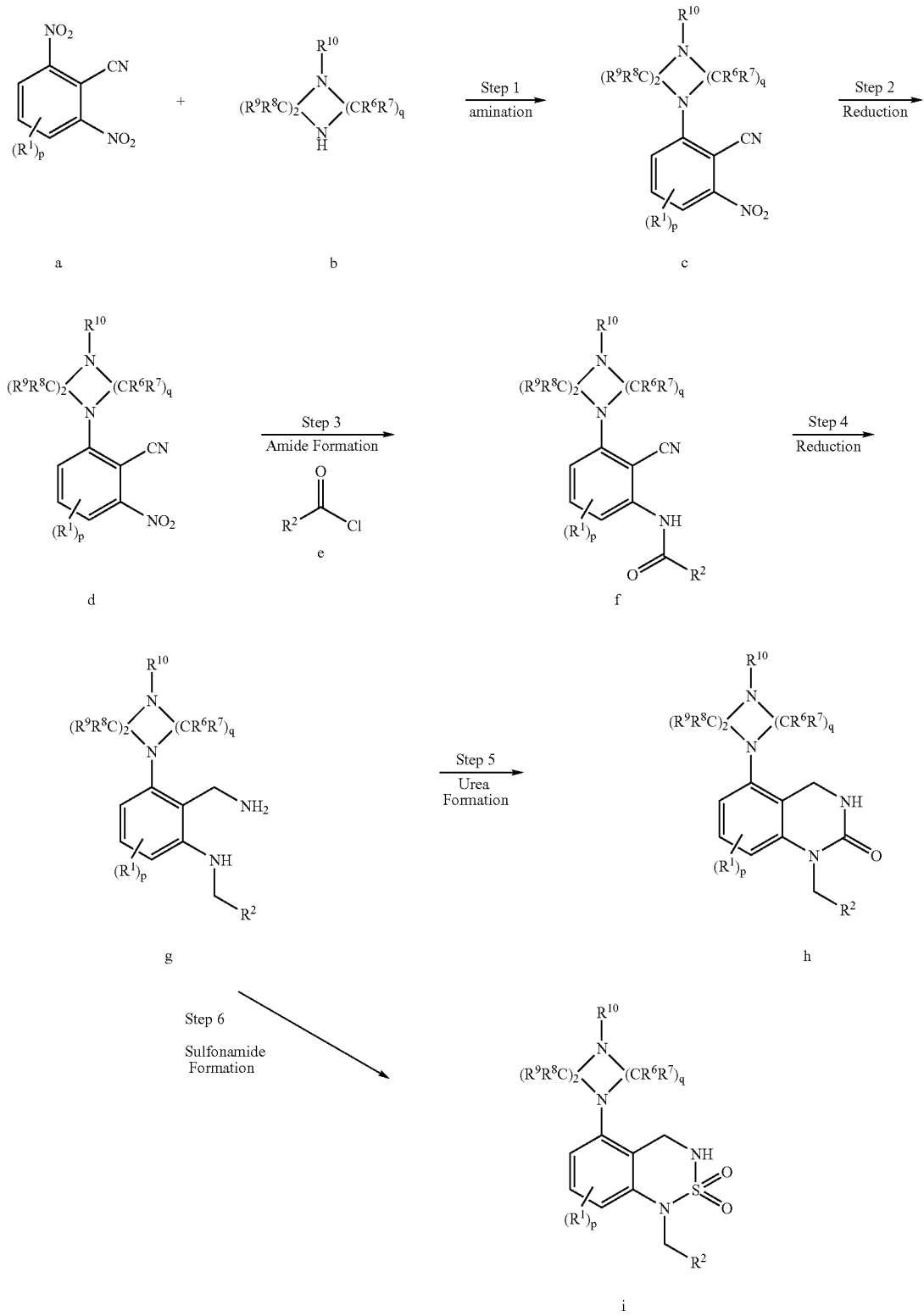

In step 1 of Scheme A, dinitrobenzonitrile a is reacted with a heterocyclic amine b to afford an amino nitrobenzonitrile c. This reaction may be effected by heating under polar aprotic solvent conditions. Where hydrogen is desired as the $R^{10}$ substituent, a BOC or other removable protecting group may be used to protect the nitrogen bound to $R^{10}$.

The amino nitrobenzonitrile c produced in step 1 is selectively reduced in step 2 to provide an aniline compound d. The reduction of step 2 may be carried out, for example, using hydrogen in the presence of palladium on activated carbon under mild pressure and ethanolic solvent conditions.

In step 3, an aryl (or heteroaryl)amide compound f is obtained by reaction of the aniline d of step 2 with an aryl (or heteroaryl) acid halide e. The reaction of step 3 may be achieved in a polar aprotic solvent such as tetrahydrofuran in the presence of triethylamine or other amine.

In step 4, aryl amide f is subject to a second, more rigorous reduction to convert the carbonyl group of compound f to a methylene, convert the nitrile group of compound f to an amine, and thus provide the benzylamine compound g. The reduction of step 4 may by carried out, for example, using boron hydride or like reducing agent under dry polar aprotic solvent conditions.

In step 5, the benzylamine g of step 4 is reacted with phosgene to provide the cyclic urea or quinazolinone compound h in accordance with the invention. The quinazolinone h is a compound of formula (I) wherein Y is carbon, X is nitrogen, Z is $-(CR^aR^b)_r-$, m, n and r are 1, and $R^3$, $R^4$, $R^5$, $R^a$ and $R^b$ are hydrogen.

As an alternative to step 5, step 6 may instead be carried out wherein benzylamine compound g is treated with sulfamide or sulfuryl chloride to form the sulfonamide compound i, Sulfonamide i is a compound of formula (I) wherein Y is sulfur, X is nitrogen, Z is $-(CR^aR^b)_r-$, m is 2, n is 1, r is 1, and $R^3$, $R^4$, $R^5$, $R^a$ and $R^b$ are hydrogen.

Numerous variations on the procedure of Scheme A are possible and will suggest themselves to those skilled in the art. For example, selective N-alkylation may be carried out using well-known techniques following step 4 or step 5 to introduce a desired $R^3$ substituent of formula (I) other than hydrogen. Selective alkylation of the benzylic carbon of compound i may also be carried out using well-known techniques to introduce an $R^4$ and/or $R^5$ substituent.

Use of benzoyl chloride ($R^2$=optionally substituted phenyl) or other benzoyl halide as the aryl halide e in step 3 provides compounds of formula (I) wherein Z is $-(CR^aR^b)_r-$, r is 1 and $R^a$ and $R^b$ are hydrogen (i.e., Z is methylene). Phenylacetyl halides or phenylpropionyl halides, such as 2-methyl-2-phenyl propionyl halide, may alternatively be used as the aryl halide e to provide compounds of formula (I) wherein r is 2 or three, and wherein one or more of $R^a$ and $R^b$ may be alkyl. As yet another alternative, an aryl (or heteroaryl)sulfonyl halide ay be used in place acid halide e to provide compounds of formula (I) wherein Z is $-SO_2-$.

In certain embodiments, heterocyclic amine b may be a piperazine of the formula j:

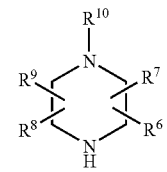

(i.e., q is 2 in formula (I)). In such instances, where $R^2$ is optionally substituted phenyl, the compound h is more specifically of the formula (V) described above. Similarly, where $R^2$ is optionally substituted phenyl, the compound i would be more specifically of the formula (VI) described above. Many substituted piperazines of this sort, including N-methyl piperazine and 3,5-dimethylpiperazine for example, are commercially available or prepared by well known techniques and may be used in the procedure of Scheme A.

Referring to Scheme B; another synthetic route for the subject compounds is shown, wherein A is a leaving group and may be the same or different on each occurrence, and p, q, $R^1$, $R^2$, $R^3$, $R^6$, $R^7$, $R^8$, $R^9$, $R^{10}$, $R^a$ and $R^b$ are as defined herein.

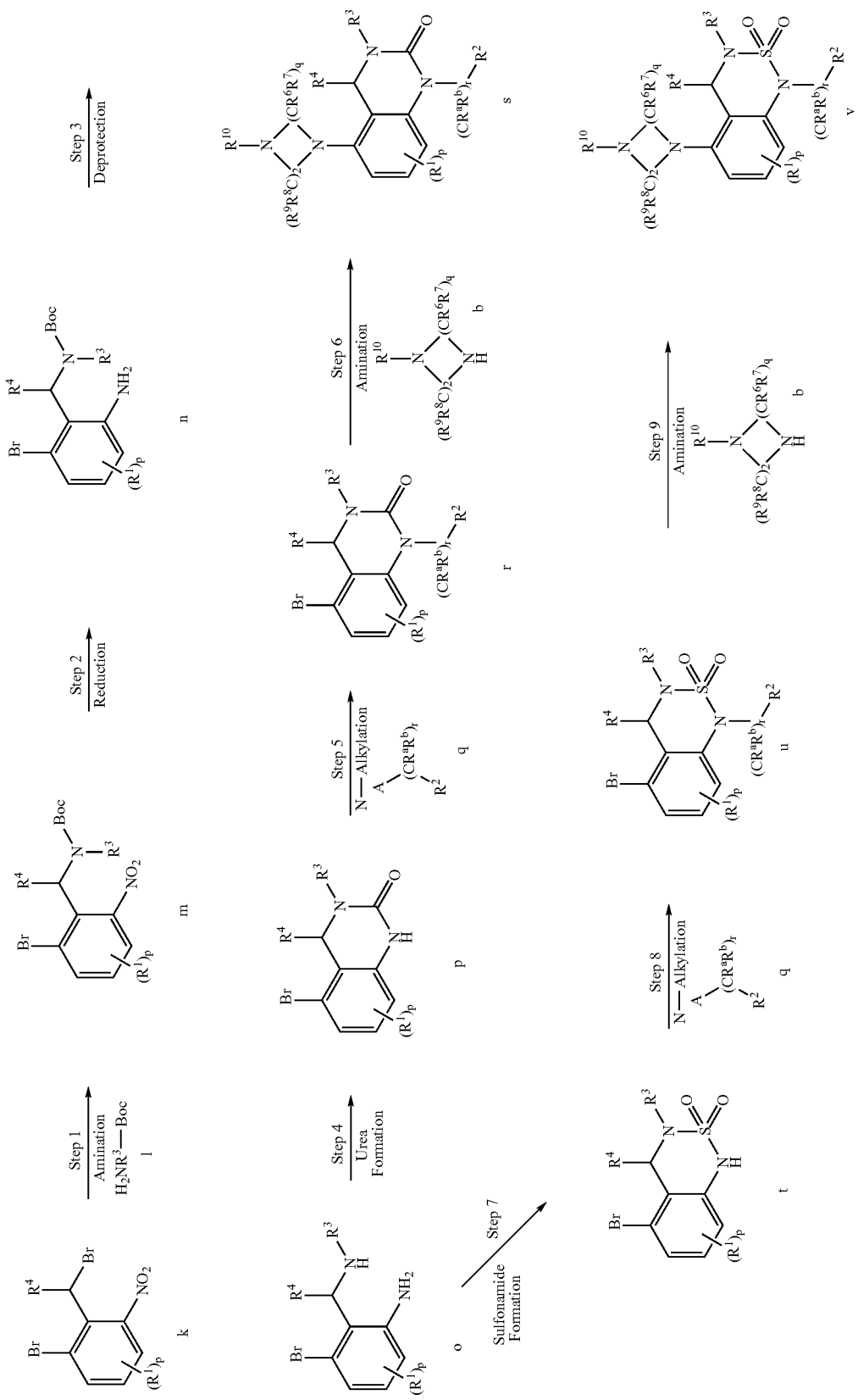

In step 1 of Scheme B, bromonitrobenzyl bromide compound k is reacted with protected amine l to yield a protected nitrobenzylamine m. This reaction may be effected in the presence of sodium hydride or other metal hydride under dry polar aprotic solvent conditions. Compound k may be prepared by treatment of the corresponding toluene with N-bromosuccinamide in the presence of benzoyl peroxide to afford the benzyl bromine.

The protected nitrobenzylamine m thus produced is reduced in step 2 to afford aniline compound n. The reduction of step 2 may be achieved using Raney nickel and hydrazine under polar protic solvent conditions.

In step 3, the benzylic amine functionality of aniline compound n is deprotected by removal of the Boc group in order to provide aminobenzylamine o. Boc removal in this step may utilize hydrochloric acid in ethanolic solvent.

The deprotected aminobenzylamine o may then undergo reaction with phosgene in step 4 to afford the cyclic urea or quinazolinone compound p. This reaction may be effected in polar aprotic solvent using triphosgen or other phosgene source.

In Step 5, an N-alkylation of the cyclic urea compound p is carried out by treatment of compound p with a strong base under dry, polar aprotic conditions, followed by reaction with an α-haloalkyl aryl compound q to provide the N-arylalkyl-quinazolinone compound r. The haloalkyl aryl compound q may comprise, for example, a benzyl halide (to provide r=1 and $R^a$ and $R^b$ as hydrogen), 3-halo-3-phenyl-propane (providing r=2 and $R^a$, $R^b$ as hydrogen), α-methylbenzyl halide (providing r=1, $R^a$ as hydrogen and $R^b$ as methyl), or other α-haloalkylphenyl halides according to the desired $R^a$ and $R^b$ substituent configuration. Compound q may also be heteroaryl in nature, such as a haloalkyl pyridine, haloalkyl thiene, haloalkyl furan, haloalkyl quinoline, or the like.

In step 6, a cross-coupling amination reaction is carried out wherein heterocyclic amine b displaces the bromine group of compound r to yield quinazolinone compound s. This reaction is facilitated in the presence of palladium catalyst and non-polar solvent conditions. The quinazolinone s is a compound of formula (I) wherein Y is carbon, X is nitrogen, Z is —$(CR^aR^b)_r$, m and n are 1, and $R^4$ and $R^5$ are hydrogen.

As an alternative to step 4, step 7 may be carried out wherein aminobenzylamine compound o is treated with sulfamide or sulfuryl chloride to form the sulfonamide compound t. Sulfonamide t may then undergo N-alkylation in step 8 by treatment with strong base followed by reaction with an α-haloalkyl aryl (or heteroaryl) compound q, in the manner described above for step 5, to provide the N-arylalkyl-sulfonamide compound u. Cross-coupling amination of the N-arylalkyl-sulfonamide compound u in step 9, in the manner described above for step 6, then affords sulfonamide compound v. Sulfonamide v is a compound of formula (I) wherein Y is sulfur, X is nitrogen, Z is —$(CR^aR^b)_r$—, m is 2, n is 1, and $R^4$ and $R^5$ are hydrogen.

It will be readily apparent that many variations on the procedure of Scheme B are possible. For example, the benzylic bromine of compound k in step 1 may be replaced by other leaving group, and the Boc group may be replaced by other removable protecting group.

The cross-coupling amination of steps 6 and 9 is shown in Scheme B as being carried out at the 5-position of the quinazolinone system, where a bromine leaving group is provided by compounds u and r. This amination reaction is effective at other ring positions as well, and thus heterocyclic amine b may also be introduced at the 6-, 7- or 8-position of the quinazoline ring system. The cross-coupling amination reaction used in steps 6 and 9 of Scheme B is described in *An Improved Catalyst System For Aromatic Carbon-Nitrogen Bond Formation: The Possible Involvement Of Bis(Phosphine) Palladium Complexes As Key Intermediates*. Wolfe et al., *J. Am. Chem. Soc.* (1996), 118(30), 7215–7216.

As in the case of Scheme A, the heterocyclic amine b used in Scheme B may be a piperazine of the formula j. In such instances, where $R^2$ is optionally substituted phenyl, r is 1 and $R^a$ and $R^b$ are hydrogen, the compound s is more specifically of the formula (V) described above. Similarly, where $R^2$ is optionally substituted phenyl, r is 1 and $R^a$ and $R^b$ are hydrogen, the compound v would be more specifically of the formula (VI) described above.

Referring now to Scheme C, there is shown another procedure that may be utilized to prepare compounds of the invention, with p, q, r, $R^2$, $R^3$, $R^6$, $R^7$, $R^8$, $R^9$, $R^{10}$, $R^a$ and $R^b$ being as defined herein. The procedure of Scheme 3 provides compounds of formula (1) wherein X is carbon instead of nitrogen.

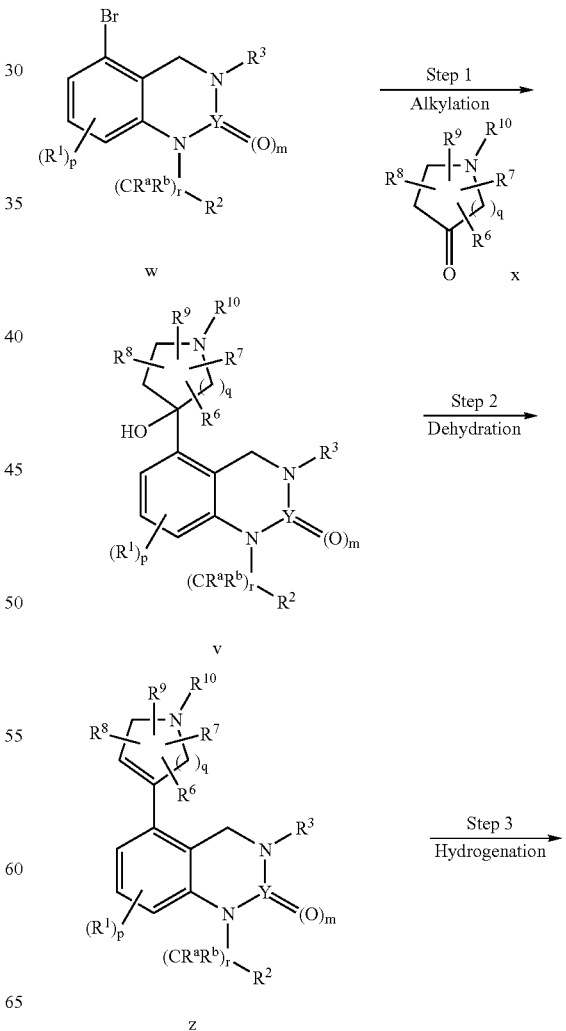

-continued

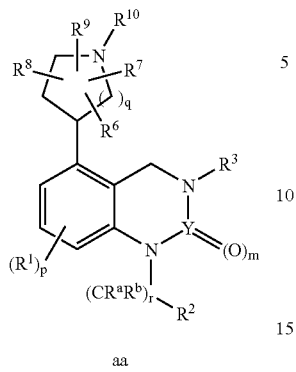

aa

In step 1 of Scheme C, quinazolinone w is treated with an alkyllithium reagent such n-butyl lithium under anhydrous polar aprotic conditions and dry ice/acetone temperature, to generate a lithiated intermediate (not shown) wherein the bromine group is replaced by lithium. This lithiated intermediate is then directly reacted in-situ with heterocyclic ketone x to effect an alkylation and provide a heterocyclyl-substituted quinazolinone y. The heterocyclic ketone x may comprise, for example, pyrrolidone (q=1) or piperidone (q=2), or azepinone (q=3) all of which are commercially available. Many substituted pyrrolidinones and piperidinones are also commercially available or are readily prepared via known synthetic routes, and may be used in this step. Where $R^{10}$ is hydrogen, Boc protection or other removable protection strategies may be used to protect the exposed nitrogen of heterocyclic ketone x and corresponding nitrogen on the heterocyclyl-substituted quinazolinone y.

In Step 2, the heterocyclyl-substituted quinazolinone y is dehydrated by treatment with mild acid to yield the compound z wherein the heterocyclyl moiety is partially unsaturated. In certain embodiments this dehydration may occur spontaneously, making step 2 unnecessary.

In Step 3, compound z of Step 3 is hydrogenated to provide quinazolinone compound aa. This reaction may be achieved via hydrogenation using a platinum or palladium catalyst under mild ethanolic conditions. The quinazolinone aa is a compound of formula (I) wherein X is carbon, Z is —$(CR^aR^b)_r$, m and n are 1, and $R^4$ and $R^5$ are hydrogen.

Yet another route to the compounds of the invention is illustrated in Scheme D, wherein p, q, $R^1$, $R^2$, $R^6$, $R^7$, $R^8$, $R^9$, $R^{10}$ $R^a$ and $R^b$ are as defined herein.

SCHEME D

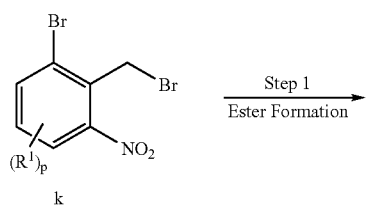

k

-continued

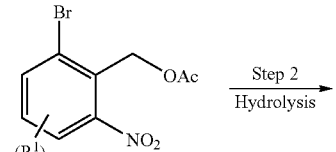

bb

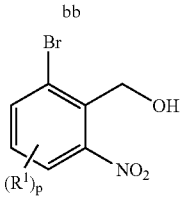

cc

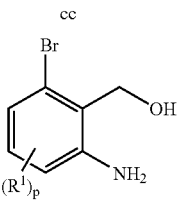

dd

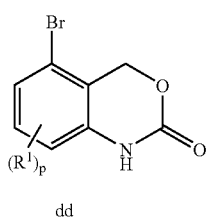

dd

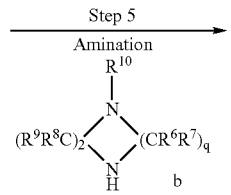

b

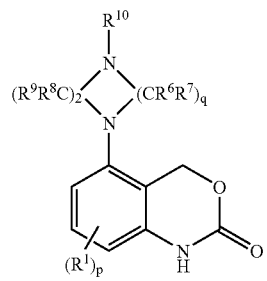

ff

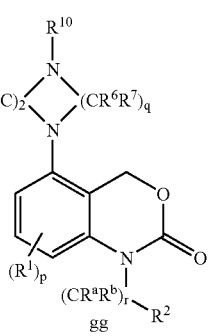

gg

In step 1 of Scheme D, bromonitrobenzyl bromide compound k is converted to nitrobenzyl ester compound bb by treatment with potassium acetate or other alkyl acetate salt under polar solvent conditions. Compound k may be prepared by treatment of the corresponding toluene with N-bromosuccinamide in the presence of benzoyl peroxide.

In step 2, bromonitrobenzyl ester bb is hydrolyzed to afford bromonitrobenzyl alcohol cc. This hydrolysis may be carried out by treatment with KOH or like base under aqueous conditions.

The bromonitrobenzyl alcohol cc may then be reduced in step 3 to yield bromoamino benzyl alcohol dd. This reduction may be achieved by treatment with Raney Nickel in the presence of hydrazine, or by treatment with other reducing agent.

In step 4, benzoxazinone compound ee is made by reaction of bromoamino benzyl alcohol dd with phosgene. This cyclization may be carried out under dry polar aprotic conditions.

In step 5, a cross-coupling amination reaction is carried out wherein heterocyclic amine b displaces the bromine group of compound ee to yield a heterocyclyl-substituted benzoxazinone ff. This reaction may be performed in the presence of palladium catalyst under non-polar solvent conditions.

In Step 6, an N-alkylation of the heterocyclyl-substituted benzoxazinone ff is carried out by treatment of compound ff with a strong base under dry, polar aprotic conditions, followed by reaction with an α-haloalkyl aryl compound q to provide the N-arylalkyl benzoxazinone compound gg. A variety of haloalkyl compounds q may be used in this step as described above in Scheme B. Compound gg is a compound of formula (I) wherein A is O, X is N, Y is C, and m is 1.

Many variations on the procedure of Scheme D are possible. In one such variation, benzoxazinone compound ee may be treated with cyclic ketone x in the manner described in Scheme C. The resulting alkylation product can then be dehydrated and reduced as shown in Scheme C to afford a compound of formula (I) wherein X is CH and A is O.

More specific details for producing compounds of formula (I) are described in the Examples section below.

Utility

The compounds of the invention have selective affinity for 5-HT receptors, including the 5-HT$_6$ the 5-HT$_{2A}$ receptor, or both, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor in radioligand binding, FLIPR and functional assays are described below.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof.

Preparation 1

Methyl-carbamic acid tert-butyl ester

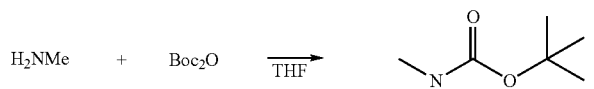

A solution of di-tert-butyldicarbonate (29.314 g, 134.27 mmol) in THF (250 ml) was cooled to 0° C. and methyl amine (71 ml, 2M in THF) was added through a funnel. After stirring at 0° C. for 2 hours, the reaction mixture was allowed to warm up to room temperature and the solvent was removed using a rotary evaporator. The resulting residue was purified by flash chromatography to give methylcarbamic acid tert-butyl ester as a pale oil (11.518g, 65%). $^1$H NMR (CDCl$_3$, 300 MHz) δ: 2.73(d, 3H, J=4.93 Hz), 1.45(s, 9H).

Preparation 2

1-Bromo-2-bromomethyl-3-nitro-benzene

A solution of 1-bromo-2-methyl-3-nitro-benzene (16.095 g, 74.5 mmol), 1-Bromo-pyrrolidine-2,5-dione (13.26 g, 74.5 mmol), benzoyl peroxide(180 mg, 0.74 mmol) in CCl$_4$ (100 ml) was heated under reflux overnight. After removing the solvent by using rotary evaporator, the residue was partitioned between water and ethyl acetate. The organic layer was washed with water and brine. After drying over MgSO$_4$, the organic fraction was concentrated in vacuo and resulting brown residue was purified by flash chromatography to give 1-bromo-2-bromomethyl-3-nitro-benzene as a yellow solid (17.55 g, 80%). $^1$H NMR (CDCl$_3$, 300 MHz) δ: 4.89(s, 2H), 7.35(dd, 1H, J1=J2=8.1 Hz), 7.88(dd, 2H, J1=1.6 Hz, J2=8.1 Hz).

Example 1

1-(4-Fluoro-benzyl)-5-piperazin-1-yl-3,4-dihydro-1H-quinazolin-2-one

The synthetic procedures described in this Example were carried out according to the process shown in Scheme E.

SCHEME E

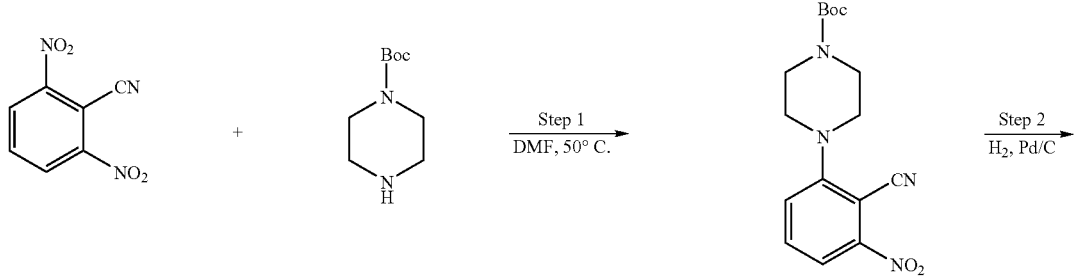

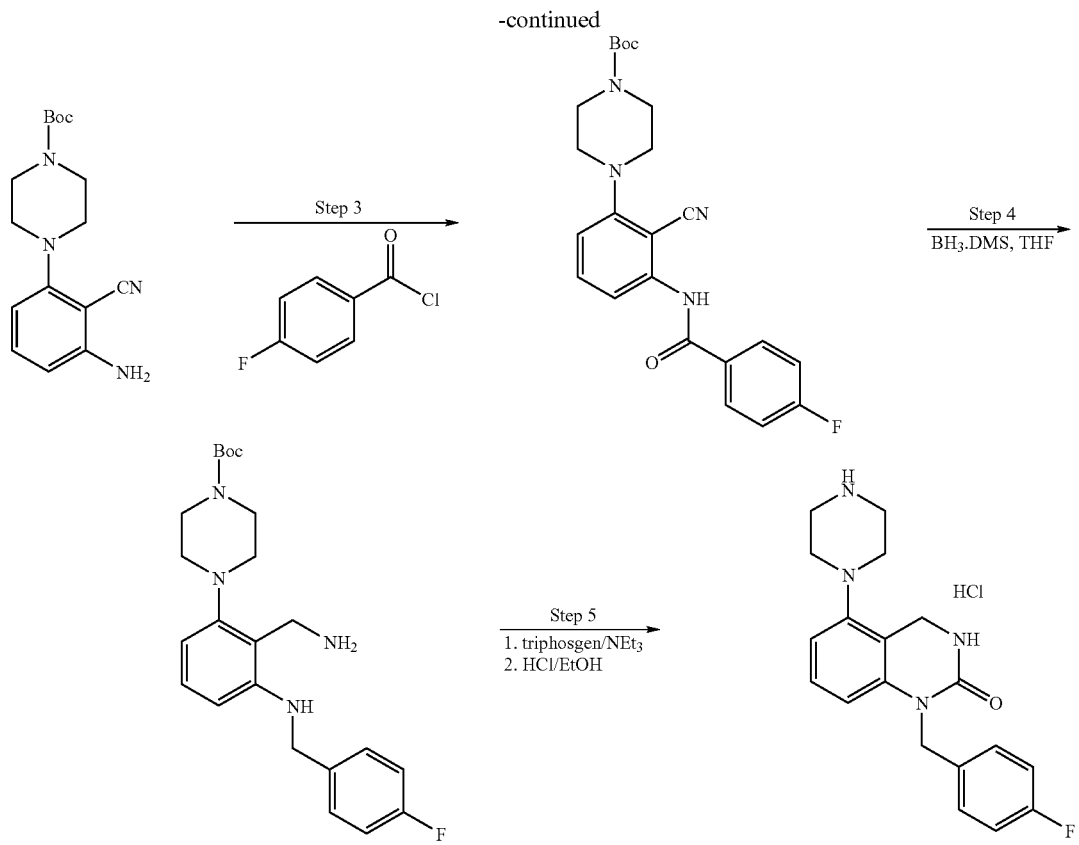

Step 1:

4-(2-Cyano-3-nitro-phenyl)-piperazine-1-carboxylic acid tert-butyl ester

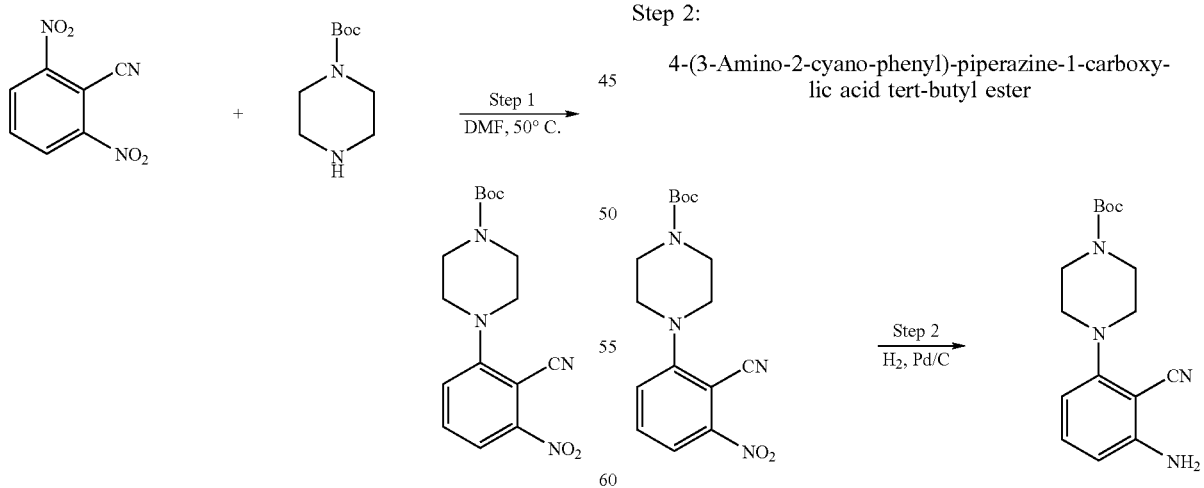

1-BOC-piperizine (piperazine-1-carboxylic acid tert-butyl ester, 20.0 g, 107.4 mmol) was added to a solution of 2,6-dinitrobenzonitrile (10.277 g, 53.2 mmol) in dry DMF (200 ml). After stirring at 50° C. overnight, the reaction mixture was cooled to room temperature and poured into a mixture of water/ethyl acetate. The organic fraction was washed with water and brine. After drying over $MgSO_4$, the organic fraction was concentrated in vacuo and the resulting brown residue was purified by flash chromatography to give 4-(2-cyano-3-nitro-phenyl)-piperazine-1-carboxylic acid tert-butyl ester as an orange solid (12.172 g, 69%). MS: $(M+H)^+$ 277.1.

Step 2:

4-(3-Amino-2-cyano-phenyl)-piperazine-1-carboxylic acid tert-butyl ester 4-(2-Cyano-3-nitro-phenyl)-piperazine-1-carboxylic acid tert-butyl ester (12.172 g, 36.6 mmol) from step 1 was dissolved in ethanol (300 ml) in a Parr flask. The flask was flushed with $N_2$, and Pd/C (1.3 g) was added. The solution was treated with $H_2$ on a Parr apparatus at 30 psi overnight. The mixture was filtered through celite, then washed with EtOAc. After concentration, the residue was purified by flash chromatography to give 4-(3-amino-2-cyano-phenyl)-piperazine-1-carboxylic acid tert-butyl ester. (7.585 g, 69%) MS: (M+H)⁺303.2.

Step 3

4-[2-Aminomethyl-3-(4-fluoro-benzylamino)-phenyl]-piperazine-1-carboxylic Acid tert-butyl ester

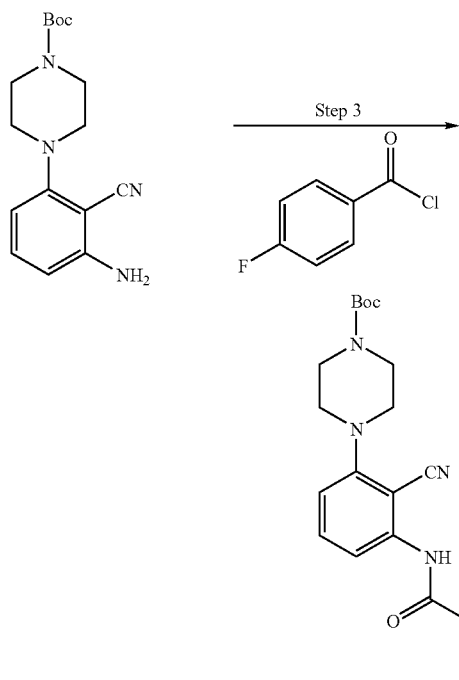

To a solution of 4-(3-Amino-2-cyano-phenyl)-piperazine-1-carboxylic acid tert-butyl ester (0.976 g, 3.23 mmol) and NEt₃ (0.9 ml, 6.48 mmol) in THF (40 ml) was added 4-fluoro-benzoyl chloride (0.42 ml, 0.355 mmol). The solution was stirred with a magnetic stirrer at room temperature overnight and the reaction mixture was partitioned between water and ethyl acetate. The organic layer was washed with water (2×30 ml) and brine (30 ml). After drying over MgSO₄, the organic fraction was concentrated in vacuo and resulting brown residue was purified by flash chromatography to give 4-[2-cyano-3-(4-fluoro-benzoylamino)-phenyl]-piperazine-1-carboxylic acid tert-butyl ester as a yellow solid (1.189 g, 87%). MS: (M+H)⁺425.2.

The following compounds were prepared in a similar fashion starting with 4-(3-Amino-2-cyano-phenyl)-piperazine-1-carboxylic acid tert-butyl ester and using various benzoyl chlorides:

4-(3-Benzoylamino-2-cyano-phenyl)-piperazine-1-carboxylic acid tert-butyl ester, MS (M+H)⁺:407.2;

4-[2-Cyano-3-(2-fluoro-benzoylamino)-phenyl]-piperazine-1-carboxylic acid tert-butyl ester, MS (M+H)⁺:425.2;

4-[2-Cyano-3-(3-fluoro-benzoylamino)-phenyl]-piperazine-1-carboxylic acid tert-butyl ester, MS (M+H)⁺:425.2;

4-[2-Cyano-3-(3-chloro-benzoylamino)-phenyl]-piperazine-1-carboxylic acid tert-butyl ester, MS (M+H)⁺: 441.2;

4-[2-Cyano-3-(2-chloro-benzoylamino)-phenyl]-piperazine-1-carboxylic acid tert-butyl ester, MS (M+H)⁺: 441.2;

4-[2-Cyano-3-(4-chloro-benzoylamino)-phenyl]-piperazine-1-carboxylic acid tert-butyl ester, MS (M+H)⁺: 441.2;

4-[2-Cyano-3-(3,4-difluoro-benzoylamino)-phenyl]-piperazine-1-carboxylic acid tert-butyl ester, MS (M+H)⁺: 443.1;

4-[2-Cyano-3-(3,4-chloro-benzoylamino)-phenyl]-piperazine-1-carboxylic acid tert-butyl ester, MS (M+H)⁺: 475.2;

4-[2-Cyano-3-(2,3-difluoro-benzoylamino)-phenyl]-piperazine-1-carboxylic acid tert-butyl ester, MS (M+H)⁺: 443.1;

4-[2-Cyano-3-(2,3-chloro-benzoylamino)-phenyl]-piperazine-1-carboxylic acid tert-butyl ester, MS (M−H)⁻: 473.2;

4-[3-(3-Chloro-2-fluoro-benzoylamino)-2-cyano-phenyl]-piperazine-1-carboxylic acid tert-butyl ester, MS (M+H)⁺:459.2;

4-[2-Cyano-3-(2-methyl-benzoylamino)-phenyl]-piperazine-1-carboxylic acid tert-butyl ester, MS (M+H)⁺: 365.2; and 4-[2-Cyano-3-(3-methyl-benzoylamino)-phenyl]-piperazine-1-carboxylic acid tert-butyl ester.

Step 4

4-[2-Aminomethyl-3-(2-fluoro-benzylamino)-phenyl]-piperazine-1-carboxylic acid tert-butyl ester

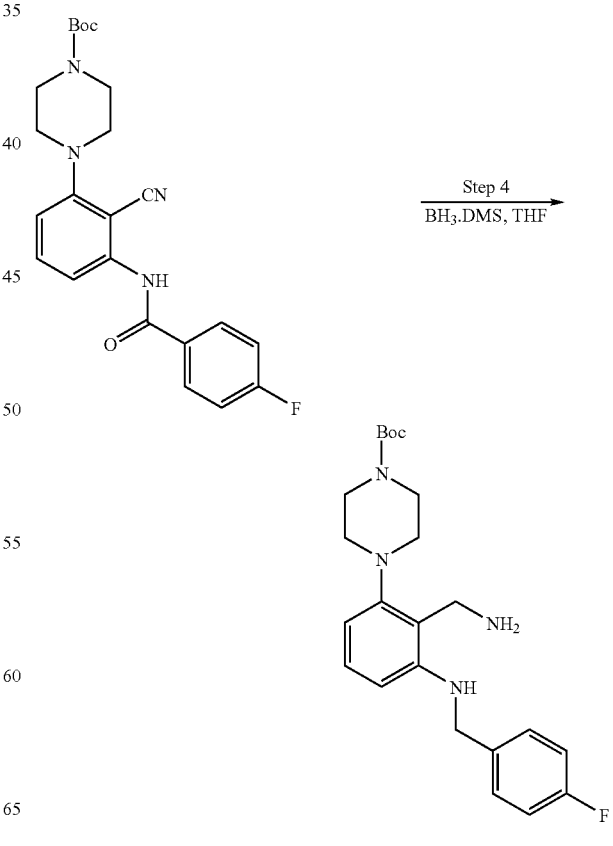

To a solution of 4-[2-cyano-3-(2-fluorobenzoylamino)-phenyl]-piperazine-1-carboxylic acid tert-butyl ester (1.282 g, 3.02 mmol) was added BH$_3$.DMS (10M in THF). After heating at 70° C. in an open flask for 20 minutes to remove the dimethyl sulfide, the reaction was then heated under reflux for 4 hours. To the cooled solution was added MeOH slowly and the resulting mixture was stirred at room temperature for an hour. The reaction mixture was partitioned between water and ethyl acetate. The organic layer was washed with water and brine. After drying over MgSO$_4$, the organic fraction was concentrated in vacuo and resulting brown residue was purified by flash chromatography to give 4-[2-aminomethyl-3-(2-fluoro-benzylamino)-phenyl]-piperazine-1-carboxylic acid tert-butyl ester as a yellow solid (858 mg, 67%). MS (M+H)$^+$:415.3

The following compounds were prepared in a similar fashion:

4-(2-Aminomethyl-3-benzylamino-phenyl)-piperazine-1-carboxylic acid tert-butyl ester. MS (M+H)$^+$:397.3;

4-[2-Aminomethyl-3-(3-fluoro-benzylamino)-phenyl]-piperazine-1-carboxylic acid tert-butyl ester. MS (M+H)$^+$: 415.3;

4-[2-Aminomethyl-3-(4-fluoro-benzylamino)-phenyl]-piperazine-1-carboxylic acid tert-butyl ester. MS (M+H)$^+$: 415.3;

4-[2-Aminomethyl-3-(2-chloro-benzylamino)-phenyl]-piperazine-1-carboxylic acid tert-butyl ester. MS (M+H)$^+$: 431.3;

4-[2-Aminomethyl-3-(3-chloro-benzylamino)-phenyl]-piperazine-1-carboxylic acid tert-butyl ester. MS (M+H)$^+$: 431.3;

4-[2-Aminomethyl-3-(4-chloro-benzylamino)-phenyl]-piperazine-1-carboxylic acid tert-butyl ester. MS (M+H)$^+$: 431.3;

4-[2-Aminomethyl-3-(2,3-difluoro-benzylamino)-phenyl]-piperazine-1-carboxylic acid tert-butyl ester. MS (M+H)$^+$: 433.2;

4-[2-Aminomethyl-3-(3,4-difluoro-benzylamino)-phenyl]-piperazine-1-carboxylic acid tert-butyl ester. MS (M+H)$^+$: 433.2;

4-[2-Aminomethyl-3-(2,3-dichloro-benzylamino)-phenyl]-piperazine-1-carboxylic acid tert-butyl ester. MS (M+H)$^+$: 465.2;

4-[2-Aminomethyl-3-(3,4-dichloro-benzylamino)-phenyl]-piperazine-1-carboxylic acid tert-butyl ester. MS (M+H)$^+$: 465.2;

4-[2-Aminomethyl-3-(3-chloro-2-fluoro-benzylamino)-phenyl]-piperazine-1-carboxylic acid tert-butyl ester. MS (M+H)$^+$:449.2;

4-[2-Aminomethyl-3-(2-methyl-benzylamino)-phenyl]-piperazine-1-carboxylic acid tert-butyl ester. MS (M+H)$^+$: 411.3; and 4-[2-Aminomethyl-3-(3-methyl-benzylamino)-phenyl]-piperazine-1-carboxylic acid tert-butyl ester.

Step 5

1-(4-Fluoro-benzyl)-5-piperazin-1-yl-3,4-dihydro-1H-quinazolin-2-one

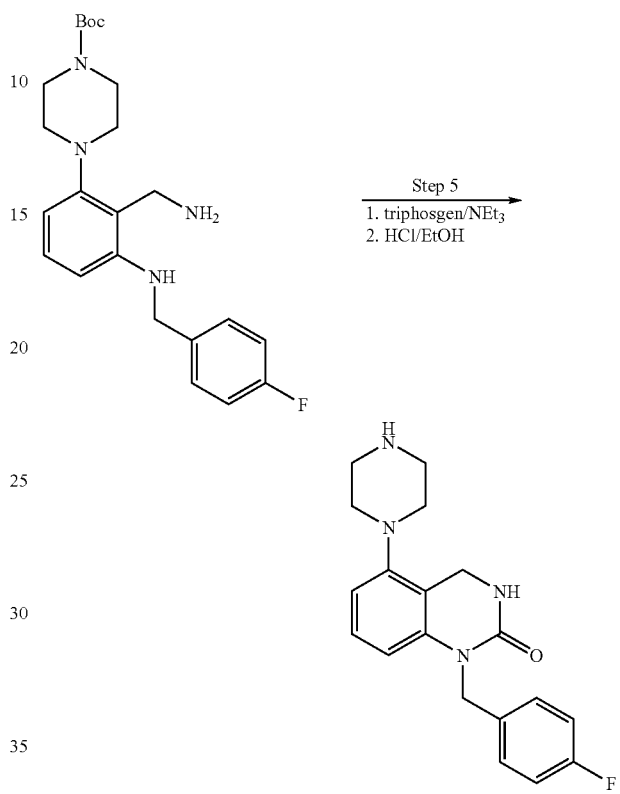

Step 5
1. triphosgen/NEt$_3$
2. HCl/EtOH

A solution of 4-[2-aminomethyl-3-(4-fluoro-benzylamino)-phenyl]-piperazine-1-carboxylic acid tert-butyl ester (255 mg, 0.62 mmol) in CH$_2$Cl$_2$(6 ml) was cooled to 0° C. and NEt$_3$(0.19 ml, 1.36 mmol) and triphosgen (64 mg, 0.22 mmol) were added. After stirring at 0° C. for half an hour, the reaction mixture was allowed to warm up to room temperature and was partitioned between water and ethyl acetate. The organic layer was washed with water and brine. After drying over MgSO$_4$, the organic fraction was concentrated in vacuo and resulting brown residue was purified by flash chromatography to give 4-[1-(4-fluoro-benzyl)-2-oxo-1,2,3,4-tetrahydro-quinazolin-5-yl]-piperazine-1-carboxylic acid tert-butyl ester as a yellow solid. (179 mg, 66%).

The 4-[1-(4-fluoro-benzyl)-2-oxo-1,2,3,4-tetrahydro-quinazolin-5-yl]-piperazine-1-carboxylic acid tert-butyl ester (179 mg, 0.41 mmol) was dissolved in 4 ml ethanol. To this solution was added 2M ethanolic hydrochloride acid solution (3 ml). The reaction mixture was heated at 100° C. for 20 minutes, at which time a crystalline solid formed. The solution was allowed to cool to room temperature and 77 mg of 1-(4-fluoro-benzyl)-5-piperazin-1-yl-3,4-dihydro-1H-quinazolin-2-one hydrochloride salt was collected as a light yellow powder. MS (M+H)$^+$:341.

The following compounds were prepared in a similar fashion:
1-(2-Fluoro-benzyl)-5-piperazin-1-yl-3,4-dihydro-1H-quinazolin-2-one hydrochloride salt. MS (M+H)$^+$:341;
1-(3-Fluoro-benzyl)-5-piperazin-1-yl-3,4-dihydro-1H-quinazolin-2-one hydrochloride salt. MS (M+H)$^+$:341;

1-(2-chloro-benzyl)-5-piperazin-1-yl-3,4-dihydro-1H-quinazolin-2-one hydrochloride salt. MS (M+H)⁺:357;

1-(3-chloro-benzyl)-5-piperazin-1-yl-3,4-dihydro-1H-quinazolin-2-one hydrochloride salt. MS (M+H)⁺:357;

1-(4-chloro-benzyl)-5-piperazin-1-yl-3,4-dihydro-1H-quinazolin-2-one hydrochloride salt. MS (M+H)⁺:357;

1-(3,4-Difluoro-benzyl)-5-piperazin-1-yl-3,4-dihydro-1H-quinazolin-2-one hydrochloride salt. MS (M+H)⁺:359;

1-(2,3-Difluoro-benzyl)-5-piperazin-1-yl-3,4-dihydro-1H-quinazolin-2-one hydrochloride salt. MS (M+H)⁺:359;

1-(2,3-Dichloro-benzyl)-5-piperazin-1-yl-3,4-dihydro-1H-quinazolin-2-one hydrochloride salt. MS (M+H)⁺:391;

1-(3,4-Dichloro-benzyl)-5-piperazin-1-yl-3,4-dihydro-1H-quinazolin-2-one hydrochloride salt. MS (M+H)⁺:391;

1-(3-Chloro-2-fluoro-benzyl)-5-piperazin-1-yl-3,4-dihydro-1H-quinazolin-2-one hydrochloride salt. MS (M+H)⁺:375;

1-(2-Methyl-benzyl)-5-piperazin-1-yl-3,4-dihydro-1H-quinazolin-2-one hydrochloride salt. MS (M+H)⁺:337; and 1-(2-Methyl-benzyl)-5-piperazin-1-yl-3,4-dihydro-1H-quinazolin-2-one, hydrochloride salt. MS (M+H)⁺:337.

Using the procedure of Example 1, but replacing 2,6-dinitro-benzonitrile in step 1 with 4-methyl-2,6-dinitro-benzonitrile, 4-ethyl-2,6-dinitro-benzonitrile, and 4-trifluoromethyl-2,6-dinitro-benzonitrile, additional compounds were prepared and are shown in Table 1.

Example 2

1-Benzyl-5-piperazin-1-yl-3,4-dihydro-1H-benzo[1,2,6]thiadiazine 2,2-dioxide

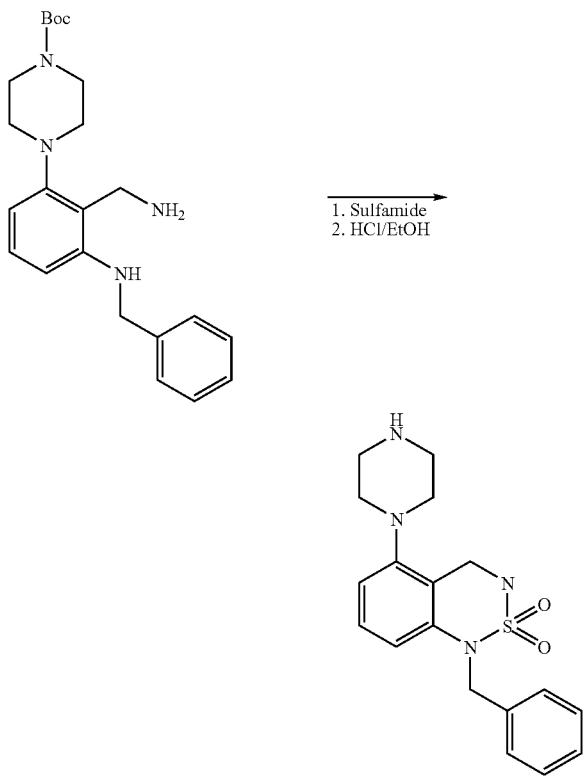

To a solution of 4-(2-aminomethyl-3-benzylamino-phenyl)-piperazine-1-carboxylic acid tert-butyl ester (245 mg, 0.62 mmol, from step 4 of Example 1) in pyridine ((6 ml) was added sulfamide (178 mg, 1:85 mmol). The reaction mixture was then heated under reflux overnight and was cooled to room temperature. 2N HCl solution and ethyl acetate were added to the mixture and the organic layer was washed with 2N HCl solution, water and brine. After drying over MgSO₄, the organic fraction was concentrated in vacuo and resulting brown residue was purified by flash chromatography to give the boc protected product as a yellow solid (124 mg, 44%). This intermediate was dissolved in 3 ml ethanol, to this solution was added 2M ethanolic hydrochloride acid solution (2 ml). The reaction mixture was heated at 100° C. for 20 minutes, at which time a crystalline solid forms. The solution was allowed to cool to room temperature and 90 mg of 1-benzyl-5-piperazin-1-yl-3,4-dihydro-1H-benzo[1,2,6]thiadiazine 2,2-dioxide hydrochloride salt was collected as an off-white powder. MS (M+H)⁺:359.

The following compounds were prepared in a similar fashion:

1-(2-Fluoro-benzyl)-5-piperazin-1-yl-3,4-dihydro-1H-benzo[1,2,6]thiadiazine 2,2-dioxide hydrochloride salt. MS (M+H)⁺:377.

1-(3-Fluoro-benzyl)-5-piperazin-1-yl-3,4-dihydro-1H-benzo[1,2,6]thiadiazine 2,2-dioxide hydrochloride salt. MS (M+H)⁺:377.

1-(4-Fluoro-benzyl)-5-piperazin-1-yl-3,4-dihydro-1H-benzo[1,2,6]thiadiazine 2,2-dioxide hydrochloride salt. MS (M+H)⁺:377.

1-(2-Chloro-benzyl)-5-piperazin-1-yl-3,4-dihydro-1H-benzo[1,2,6]thiadiazine 2,2-dioxide hydrochloride salt. MS (M+H)⁺:393.

1-(3-Chloro-benzyl)-5-piperazin-1-yl-3,4-dihydro-1H-benzo[1,2,6]thiadiazine 2,2-dioxide hydrochloride salt. MS (M+H)⁺:393.

1-(4-Chloro-benzyl)-5-piperazin-1-yl-3,4-dihydro-1H-benzo[1,2,6]thiadiazine 2,2-dioxide hydrochloride salt. MS (M+H)⁺:393.

1-(2,3-Difluoro-benzyl)-5-piperazin-1-yl-3,4-dihydro-1H-benzo[1,2,6]thiadiazine 2,2-dioxide hydrochloride salt. MS (M+H)⁺:395.

1-(3,4-Difluoro-benzyl)-5-piperazin-1-yl-3,4-dihydro-1H-benzo[1,2,6]thiadiazine 2,2-dioxide hydrochloride salt. MS (M+H)⁺:395.

1-(2,3-Dichloro-benzyl)-5-piperazin-1-yl-3,4-dihydro-1H-benzo[1,2,6]thiadiazine 2,2-dioxide hydrochloride salt. MS (M+H)⁺:427.

1-(3,4-Dichloro-benzyl)-5-piperazin-1-yl-3,4-dihydro-1H-benzo[1,2,6]thiadiazine 2,2-dioxide hydrochloride salt. MS (M+H)⁺:427.

1-(3-Chloro-2-fluoro-benzyl)-5-piperazin-1-yl-3,4-dihydro-1H-benzo[1,2,6]thiadiazine 2,2-dioxide hydrochloride salt. MS (M+H)⁺:411; and 1-(2-Methyl-benzyl)-5-piperazin-1-yl-3,4-dihydro-1H-benzo[1,2,6]thiadiazine 2,2-dioxide hydrochloride salt. MS (M+H)⁺:373.

Example 3

1-(3-Fluoro-benzyl)-3-methyl-5-piperazin-1-yl-3,4-dihydro-1H-quinazolin-2-one

The synthetic procedures described in this Example were carried out according to the process shown in Scheme F.

SCHEME F

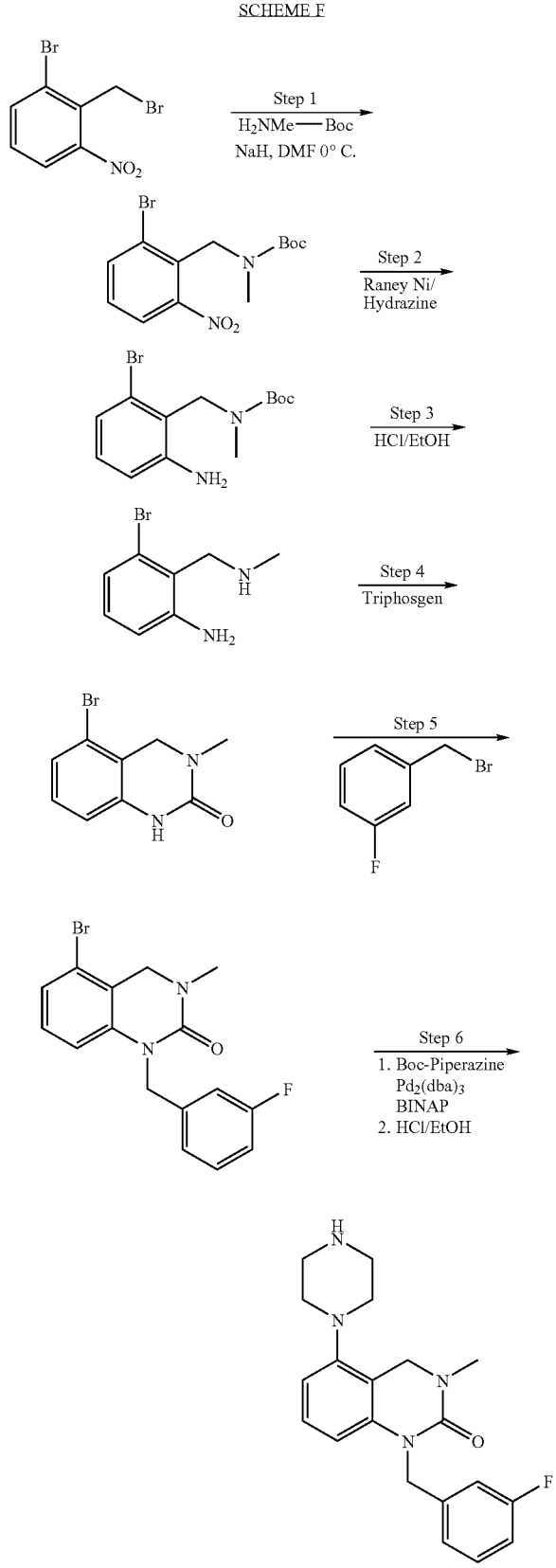

Step 1

(2-Bromo-6-nitro-benzyl)-methyl-carbamic acid tert-butyl ester

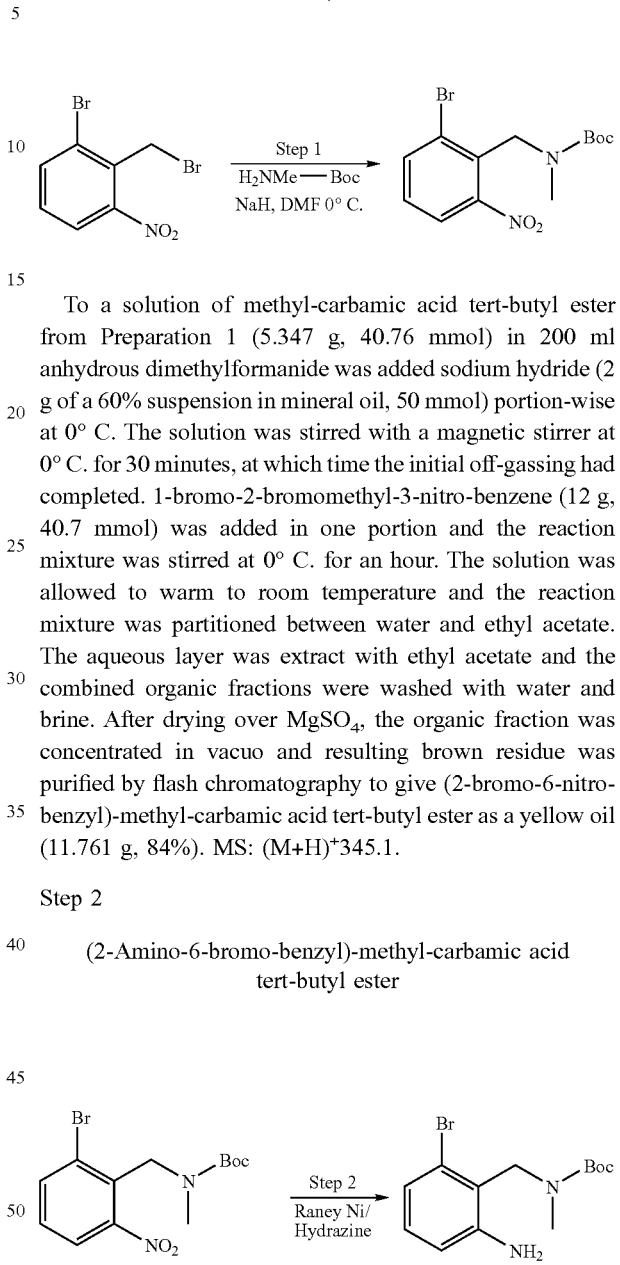

To a solution of methyl-carbamic acid tert-butyl ester from Preparation 1 (5.347 g, 40.76 mmol) in 200 ml anhydrous dimethylformanide was added sodium hydride (2 g of a 60% suspension in mineral oil, 50 mmol) portion-wise at 0° C. The solution was stirred with a magnetic stirrer at 0° C. for 30 minutes, at which time the initial off-gassing had completed. 1-bromo-2-bromomethyl-3-nitro-benzene (12 g, 40.7 mmol) was added in one portion and the reaction mixture was stirred at 0° C. for an hour. The solution was allowed to warm to room temperature and the reaction mixture was partitioned between water and ethyl acetate. The aqueous layer was extract with ethyl acetate and the combined organic fractions were washed with water and brine. After drying over MgSO$_4$, the organic fraction was concentrated in vacuo and resulting brown residue was purified by flash chromatography to give (2-bromo-6-nitro-benzyl)-methyl-carbamic acid tert-butyl ester as a yellow oil (11.761 g, 84%). MS: (M+H)$^+$345.1.

Step 2

(2-Amino-6-bromo-benzyl)-methyl-carbamic acid tert-butyl ester

To a warm solution of (2-bromo-6-nitro-benzyl)-methyl-carbamic acid tert-butyl ester from Preparation 2 (589 mg, 1.71 mmol), and a small (catalytic) amount of Ra(Ni) in THF/MeOH (8 ml/9 ml) was added H$_2$NNH$_2$ (110 µl, 3.5 mmol). With stirring, the solution was heated under reflux for an hour and was allowed to cool to room temperature. The reaction mixture was filtered through celite and washed with ethyl acetate. The concentrated filtrate was purified by flash chromatography to give (2-amino-6-bromo-benzyl)-methyl-carbamic acid tert-butyl ester (371 mg, 69%). $^1$H NMR (CDCl$_3$, 300 MHz) δ:1.48(s, 9H), 2.80(s, 3H), 4.67(s, 2H), 6.56(m, 1H), 6.90(m, 2H).

Step 3

3-Bromo-2-methylaminomethyl-phenylamine

(2-Amino-6-bromo-benzyl)-methyl-carbamic acid tert-butyl ester (371 mg) was dissolved in 50 ml ethanol. To this solution was added 2M ethanolic hydrochloride acid solution (10 ml). The reaction mixture was heated at 100° C. for 30 minutes, at which time the deprotection was completed. The solution was allowed to cool to room temperature and poured into the mixture of saturated $NaHCO_3$ solution and ethyl acetate. The aqueous layer was extracted with EtOAc three times and the organic fractions were concentrated to give 3-bromo-2-methylaminomethyl-phenylamine as a brown oil (1.938 g, 76%). MS: $(M+H)^+$ 217.1.

Step 4

5-Bromo-3-methyl-3,4-dihydro-1H-quinazolin-2-one

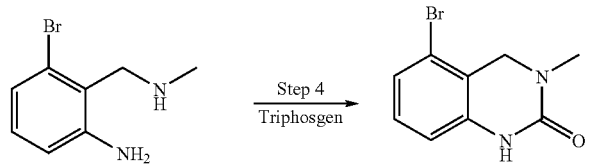

To a solution of 3-bromo-2-methylaminomethyl-phenylamine (1.153 g, 5.36 mmol) in $CH_2Cl_2$ (50 ml) was added $NEt_3$ (1.5 ml, 10.76 mmol), triphosgen (555 mg, 1.87 mmol) at 0° C. The reaction was allowed to warm up to room temperature and stirred overnight. After the solvent was removed by using a rotary evaporator, the residue was partitioned between water and ethyl acetate. The organic layer was washed by $H_2O$ and brine. After drying over $MgSO_4$, the organic fraction was concentrated in vacuo and resulting brown residue was purified by flash chromatography to give 5-bromo-3-methyl-3,4-dihydro-1H-quinazolin-2-one as white solid. (650 mg, 50%) MS: $(M+H)^+$ 241.1.

Step 5

5-Bromo-1-(3-fluoro-benzyl)-3-methyl-3,4-dihydro-1H-quinazolin-2-one

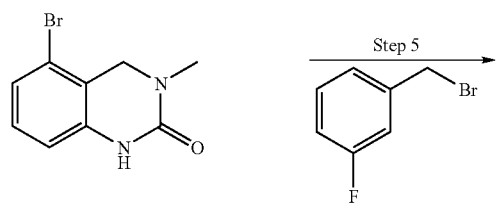

-continued

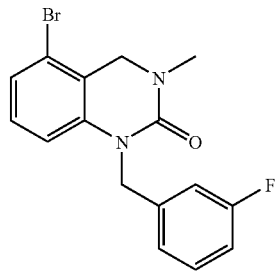

To a solution of 5-bromo-3-methyl-3,4-dihydro-1H-quinazolin-2-one (132 mg, 0.55 mmol) in 5 ml anhydrous dimethylformanide was added sodium hydride (33 mg of a 60% suspension in mineral oil, 0.83 mmol) portionwise at 0° C. The solution was stirred with a magnetic stirrer at 0° C. for 20 minutes, at which time the initial offgassing ended. 3-Fluorobenzyl bromide (0.08 ml, 0.65 mmol) was added in one portion and the reaction mixture was stirred at 0° C. for an hour. The solution was allowed to warm to room temperature and the reaction mixture was partitioned between water and ethyl acetate. The aqueous layer was extracted with ethyl acetate and the combined organic fractions were washed with water and brine. After drying over $MgSO_4$, the organic fraction was concentrated in vacuo and resulting residue was purified by flash chromatography to give 156 mg of 5-bromo-1-(3-fluoro-benzyl)-3-methyl-3,4-dihydro-1H-quinazolin-2-one as a yellow solid (81%). MS: 349.1 $(M+H)^+$.

The following compounds were prepared in a similar fashion:

1-Benzyl-5-bromo-3-methyl-3,4-dihydro-1H-quinazolin-2-one. MS: 333.0 $(M+H)^+$.

5-Bromo-1-(2-fluoro-benzyl)-3-methyl-3,4-dihydro-1H-quinazolin-2-one. MS: 349.1 $(M+H)^+$.

5-Bromo-1-(4-fluoro-benzyl)-3-methyl-3,4-dihydro-1H-quinazolin-2-one. MS: 351.1 $(M+H)^+$.

3-(5-Bromo-3-methyl-2-oxo-3,4-dihydro-2H-quinazolin-1-ylmethyl)-benzonitrile. MS: 356.1 $(M+H)^+$.

Step 6

1-(3-Fluoro-benzyl)-3-methyl-5-piperazin-1-yl-3,4-dihydro-1H-quinazolin-2-one

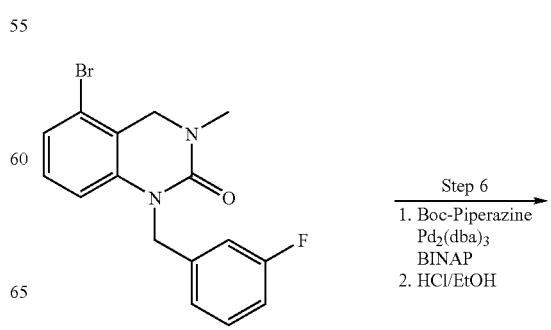

-continued

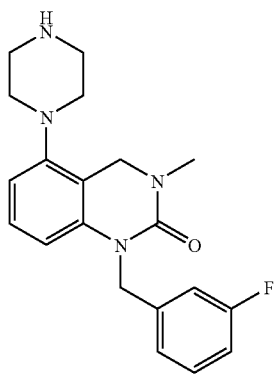

A solution of 5-bromo-1-(3-fluoro-benzyl)-3-methyl-3,4-dihydro-1H-quinazolin-2-one (156 mg, 0.45 mmol) and 1-Boc-piperazine (100 mg, 0.54 mmol) in 1 ml toluene was added to a mixture of Pd$_2$(dba)$_3$ (8 mg, 0.009 mmol), BINAP (2,2'-bis(diphenylphosphino)-1,1'-binaphthyl (14 mg, 0.022 mmol), and NaOt-Bu (65 mg, 0.67 mmol). With stirring, the solution was heated at 95° C.–100° C. for 1 hour and was allowed to cool to room temperature. The reaction mixture was filtered through celite and washed with ethyl acetate. The filtrate was washed with water and brine. After drying over MgSO$_4$, the organic fraction was concentrated in vacuo and resulting brown residue was purified by prep TLC to give 72 mg 4-[1-(3-fluoro-benzyl)-3-methyl-2-oxo-1,2,3,4-tetrahydro-quinazolin-5-yl]-piperazine-1-carboxylic acid tert-butyl ester as yellow solid (75 mg, 35%).

The 4-[1-(3-fluoro-benzyl)-3-methyl-2-oxo-1,2,3,4-tetrahydro-quinazolin-5-yl]-piperazine-1-carboxylic acid tert-butyl ester (75 mg, 0.16 mmol) was dissolved in 4 ml ethanol. To this solution was added 2 M ethanolic hydrochloric acid solution (2 ml.) The reaction mixture was heated at 100° C. for 20 minutes, at which time a crystalline solid formed. The solution was allowed to cool to room temperature and 45 mg of 1-(3-fluorobenzyl)-3-methyl-5-piperazin-1-yl-3,4-dihydro-1H-quinazolin-2-one hydrochloride salt was collected as a light yellow powder. MS: 355 (M+H)$^+$.

The following compounds were similarly prepared:

1-Benzyl-3-methyl-5-piperazin-1-yl-3,4-dihydro-1H-quinazolin-2-one hydrochloride salt. MS: 337 (M+H)$^+$;

1-(2-Fluoro-benzyl)-3-methyl-5-piperazin-1-yl-3,4-dihydro-1H-quinazolin-2-one hydrochloride salt. MS: 355 (M+H)$^+$;

1-(4-Fluoro-benzyl)-3-methyl-5-piperazin-1-yl-3,4-dihydro-1H-quinazolin-2-one hydrochloride salt. MS: 355 (M+H)$^+$; and 3-(3-Methyl-2-oxo-5-piperazin-1-yl-3,4-dihydro-2H-quinazolin-1-ylmethyl)-benzonitrile hydrochloride salt. MS: 362 (M+H)$^+$.

Using the appropriate protected amines in step 1 in place of methyl-carbamic acid tert-butyl ester, the following compounds were prepared.

3-Ethyl-1-(4-fluoro-benzyl)-5-piperazin-1-yl-3,4-dihydro-1H-quinazolin-2-one hydrochloride salt. MS: 368 (M+H)$^+$;

2-(1-Benzyl-2-oxo-5-piperazin-1-yl-1,4-dihydro-2H-quinazolin-3-yl)-acetamide hydrochloride salt. MS: 379 (M+H)$^+$;

1-Benzyl-3-ethyl-5-piperazin-1-yl-3,4-dihydro-1H-quinazolin-2-on hydrochloride salt. MS: 350 (M+H)$^+$;

2-[1-(3-Fluoro-benzyl)-2-oxo-5-piperazin-1-yl-1,4-dihydro-2H-quinazolin-3-yl]-acetamide hydrochloride salt. MS: 398 (M+H)$^+$;

1-Benzyl-3-isopropyl-5-piperazin-1-yl-3,4-dihydro-1H-quinazolin-2-one hydrochloride salt. MS: 364 (M+H)$^+$;

1-(2-Fluoro-benzyl)-3-isopropyl-5-piperazin-1-yl-3,4-dihydro-1H-quinazolin-2-one hydrochloride salt. MS: 382 (M+H)$^+$;

1-(3-Chloro-benzyl)-3-isopropyl-5-piperazin-1-yl-3,4-dihydro-1H-quinazolin-2-one hydrochloride salt. MS: 398 (M+H)$^+$;

1-(2,3-Difluoro-benzyl)-3-isopropyl-5-piperazin-1-yl-3,4-dihydro-1H-quinazolin-2-one hydrochloride salt. MS: 400 (M+H)$^+$;

1-(4-Fluoro-benzyl)-3-isopropyl-5-piperazin-1-yl-3,4-dihydro-1H-quinazolin-2-one hydrochlor salt. MS: 382 (M+H)$^+$; and 1-(3-Fluoro-benzyl)-3-isopropyl-5-piperazin-1-yl-3,4-dihydro-1H-quinazolin-2-one hydrochloride salt. MS: 382 (M+H)$^+$;.

Example 4

1-Benzyl-3-methyl-5-piperazin-1-yl-3,4-dihydro-1H-benzo[1,2,6]thiadiazine 2,2-dioxide hydrochloride salt. MS: 373 (M+H)$^+$ The synthetic procedures described in this Example were carried out according to the process shown in Scheme G.

SCHEME G

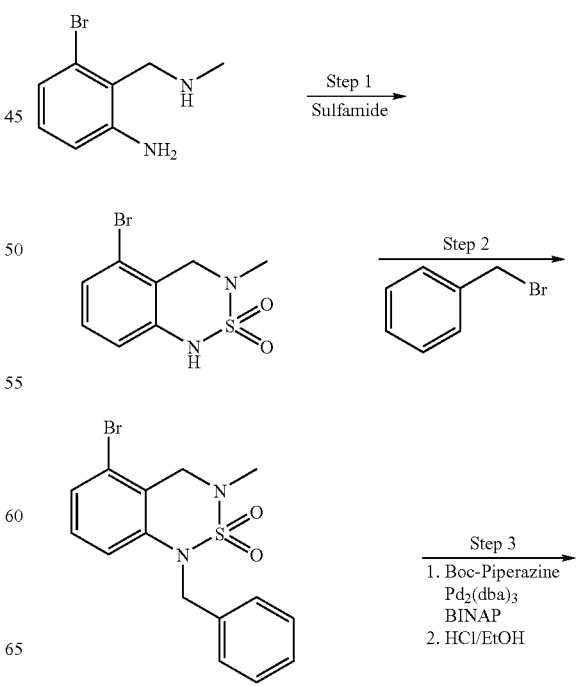

-continued

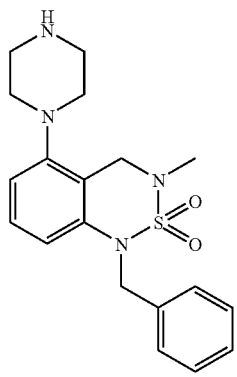

Step 1

5-Bromo-3-methyl-3,4-dihydro-1H-benzo[1,2,6]thiadiazine 2,2-dioxide

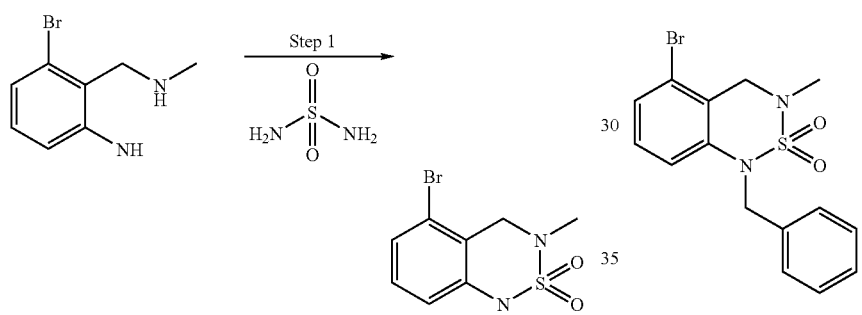

To a solution of 3-bromo-2-methylaminomethyl-phenylamine from step 3 of Example 3 (2.615 g, 12.2 mmol) in pyridine (50 ml) was added sulfamide (3.5 g, 36.4 mmol). The solution was heated under reflux overnight, and the cooled reaction mixture was partitioned between 2N HCl water solution and ethyl acetate. The organic layer was washed with 2N HCl solution, water, brine. After drying over MgSO$_4$, the organic fraction was concentrated in vacuo and resulting brown residue was purified by flash chromatography to give 5-bromo-3-methyl-3,4-dihydro-1H-benzo[1,2,6]thiadiazine 2,2-dioxide as a white solid. (2.32 g, 69%) MS: (M+H)$^+$277.1.

Step 2

1-Benzyl-5-bromo-3-methyl-3,4-dihydro-1H-benzo[1,2,6]thiadiazine 2,2-dioxide

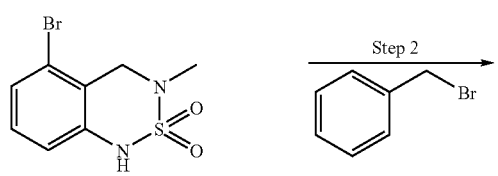

-continued

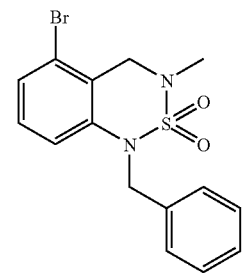

The benzylation procedure of step 5 of Example 3 was used to afford 1-Benzyl-5-bromo-3-methyl-3,4-dihydro-1H-benzo[1,2,6]thiadiazine 2,2-dioxide. MS: 367.0 (M+H)$^+$.

Step 3

1-Benzyl-3-methyl-5-piperazin-1-yl-3,4-dihydro-1H-benzo[1,2,6]thiadiazine 2,2-dioxide

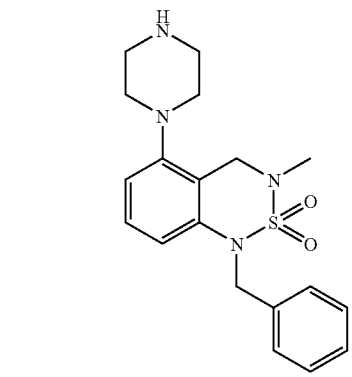

The cross-coupling amination procedure of step 6 of Example 3 was used to afford 1-benzyl-3-methyl-5-piperazin-1-yl-3,4-dihydro-1H-benzo[1,2,6]thiadiazine 2,2-dioxide MS: 373 (M+H)$^+$.

Example 5

1-Benzyl-5-piperazin-1-yl-1,4-dihydro-benzo[d][1,3]oxazin-2-one

The synthetic procedures described in this Example were carried out according to the process shown in Scheme H.

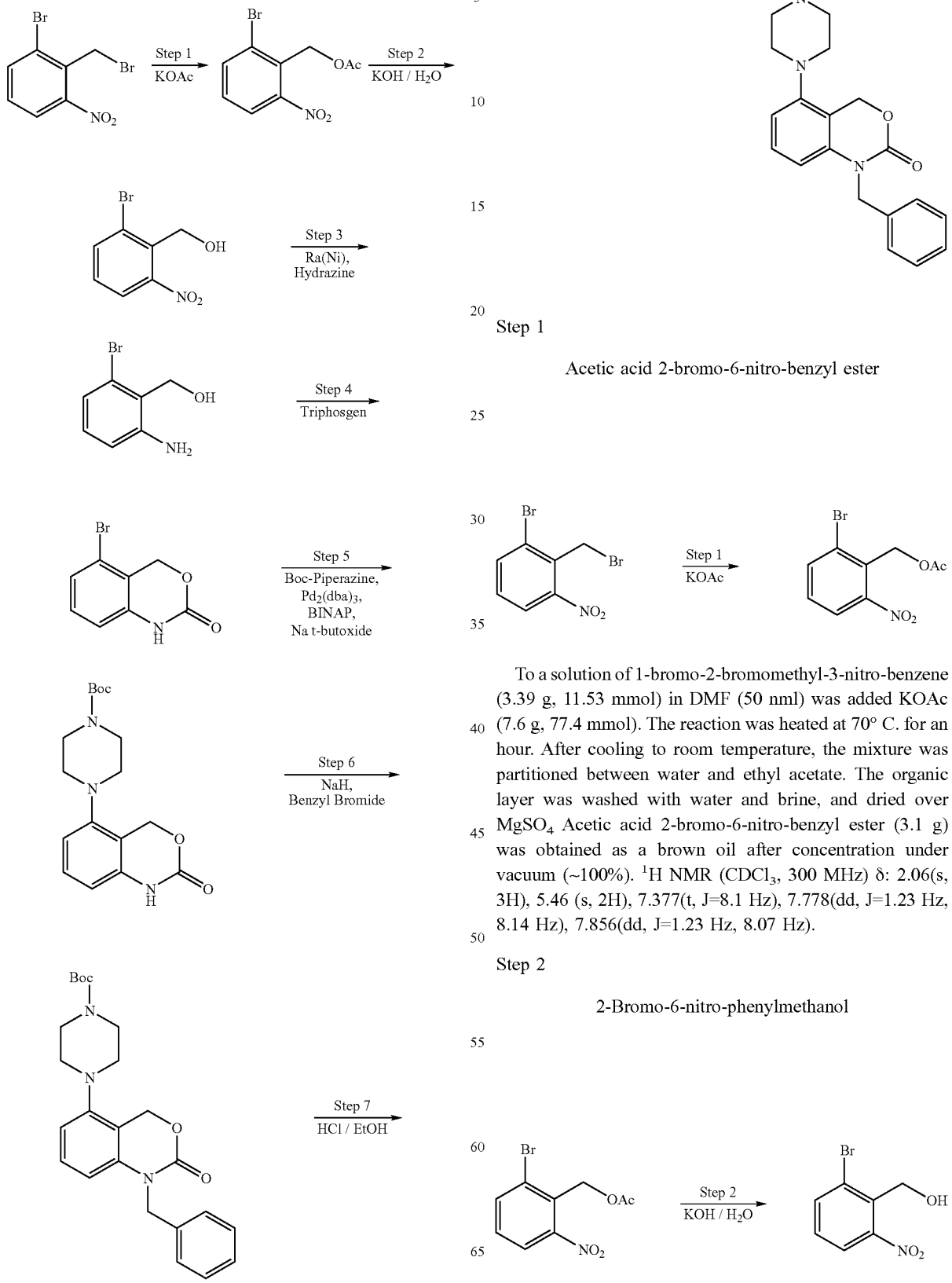

Step 1

Acetic acid 2-bromo-6-nitro-benzyl ester

To a solution of 1-bromo-2-bromomethyl-3-nitro-benzene (3.39 g, 11.53 mmol) in DMF (50 nml) was added KOAc (7.6 g, 77.4 mmol). The reaction was heated at 70° C. for an hour. After cooling to room temperature, the mixture was partitioned between water and ethyl acetate. The organic layer was washed with water and brine, and dried over $MgSO_4$ Acetic acid 2-bromo-6-nitro-benzyl ester (3.1 g) was obtained as a brown oil after concentration under vacuum (~100%). $^1$H NMR ($CDCl_3$, 300 MHz) δ: 2.06(s, 3H), 5.46 (s, 2H), 7.377(t, J=8.1 Hz), 7.778(dd, J=1.23 Hz, 8.14 Hz), 7.856(dd, J=1.23 Hz, 8.07 Hz).

Step 2

2-Bromo-6-nitro-phenylmethanol

To a solution of acetic acid 2-bromo-6-nitro-benzyl ester (536 mg, 1.96 mmol) in water (20 ml) was added KOH solution (10%, 1.5 ml). The reaction was heated under reflux overnight. After cooling to room temperature, the reaction mixture was extracted with ethyl acetate. The combined extracts were treated with MgSO$_4$, and concentrated under vacuum to give (2-bromo-6-nitro-phenyl)-methanol (389 mg, 86%) as a yellow solid. $^1$H NMR (CDCl$_3$, 300 MHz) δ: 4.93 (d, J=7.43 Hz), 7.354 (t, J=8.10 Hz), 7.84 (dd, J=1.23 Hz, 8.17 Hz), 7.89(dd, J=1.22 Hz, 8.03 Hz).

Step 3

(2-Amino-6-bromo-phenyl)-methanol

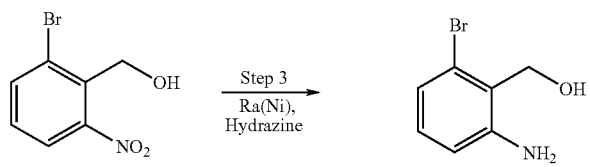

To a warm solution of (2-bromo-6-nitro-phenyl)-methanol (751 mg, 3.24 mmol), and a catalytic amount of Raney (Ni) in THF/MeOH (10 ml/10 ml) was added H$_2$NNH$_2$ (0.2 ml, 6.37 mmol). With stirring, the solution was heated under reflux for an hour and was allowed to cool to room temperature. The reaction mixture was filtered through celite and washed with ethyl acetate. The concentrated filtrate was purified by flash chromatography to give (2-amino-6-bromo-phenyl)-methanol (549 mg, 84%). MS: 202.1 (M+H)$^+$.

Step 4

5-Bromo-1,4-dihydro-benzo[d][1,3]oxazin-2-one

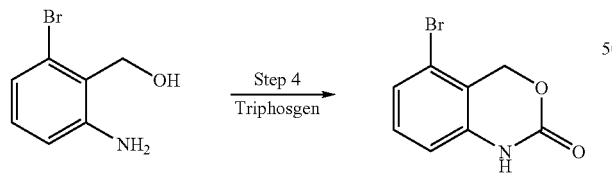

A solution of (2-Amino-6-bromo-phenyl)-methanol (549 mg, 2.72 mmol) and triphosgen (282 mg, 0.95 mmol) in THF (20 ml) was heated at 50° C. for an hours. After cooling to room temperature, the reaction mixture was partitioned between water and ethyl acetate. The organic layer was washed by water and brine. After drying over MgSO$_4$, the solution was concentrated under vacuum to give 5-bromo-1,4-dihydro-benzo[d][1,3]oxazin-2-one (582 mg, 94%) as a white solid. MS: 226.1 (M−H)$^-$. (M+H)$^-$.

Step 5

4-(2-Oxo-1,4-dihydro-2H-benzo[d][1,3]oxazin-5-yl)-piperazine-1-carboxylic acid tert-butyl

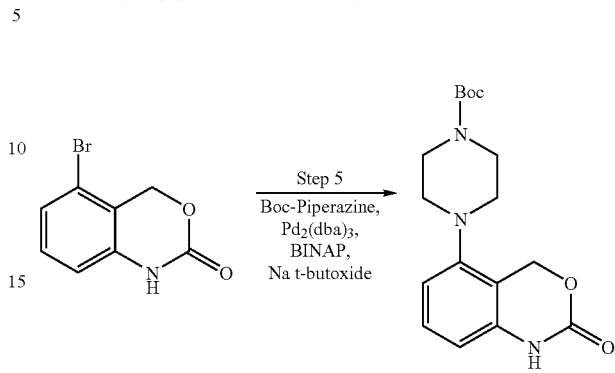

A solution of 5-bromo-1,4-dihydro-benzo[d][1,3]oxazin-2-one (96 mg, 0.42 mmol) and 1-Boc-piperazine (100 mg, 0.54 mmol) in 2 ml toluene was added to a mixture of Pd$_2$(dba)$_3$ (8 mg, 0.009 mmol), BINAP (13 mg, 0.022 mmol), NaOt-Bu (121 mg, 1.26 mmol). With stirring, the solution was heated at 95° C.–100° C. for 4 hours and was allowed to cool to room temperature. The reaction mixture was filtered through celite and washed with ethyl acetate. The filtrate was washed with water and brine. After drying over MgSO$_4$, the organic fraction was concentrated in vacuo and the resulting brown residue was purified by prep TLC to give 43 mg 4-(2-oxo-1,4-dihydro-2H-benzo[d][1,3]oxazin-5-yl)-piperazine-1-carboxylic acid tert-butyl ester as a yellow solid (31%).

Step 6

1-Benzyl-5-piperazin-1-yl-1,4-dihydro-benzo[d][1,3]oxazin-2-one

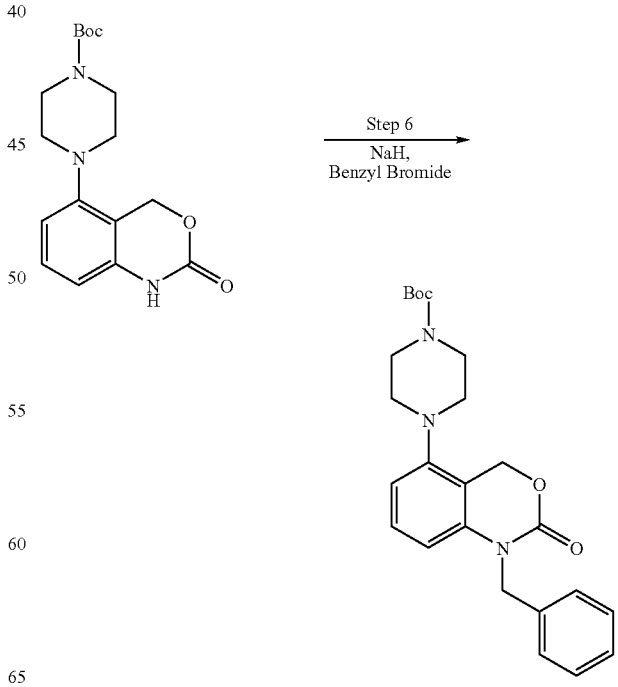

To a solution of 4-(2-oxo-1,4-dihydro-2H-benzo[d][1,3] oxazin-5-yl)-piperazine-1-carboxylic acid tert-butyl ester (43 mg, 0.13 mmol) in 2 ml anhydrous dimethylformamide was added sodium hydride (8 mg of a 60% suspension in mineral oil, 0.2 mmol) portion-wise at 0° C. The solution was stirred with a magnetic stirrer at 0° C. for 20 minutes, at which time the initial off-gassing ended. Benzyl bromide (0.02 ml, 0.17 mmol) was added in one portion and the reaction mixture was stirred at 0° C. for an hour. The solution was allowed to warm to room temperature and the reaction mixture was partitioned between water and ethyl acetate. The aqueous layer was extracted with ethyl acetate and the combined organic fractions were washed with water and brine. After drying over MgSO$_4$, the organic fraction was concentrated in vacuo and resulting brown residue was purified by prep TLC to give 33 mg of 4-(1-benzyl-2-oxo-1,4-dihydro-2H-benzo[d] [1,3]oxazin-5-yl)-piperazine-1-carboxylic acid tert-butyl ester as a white solid (60%). MS: 424 (M+H)$^+$.

Step 7

1-Benzyl-5-piperazin-1-yl-1,4-dihydro-benzo[d][13] oxazin-2-one

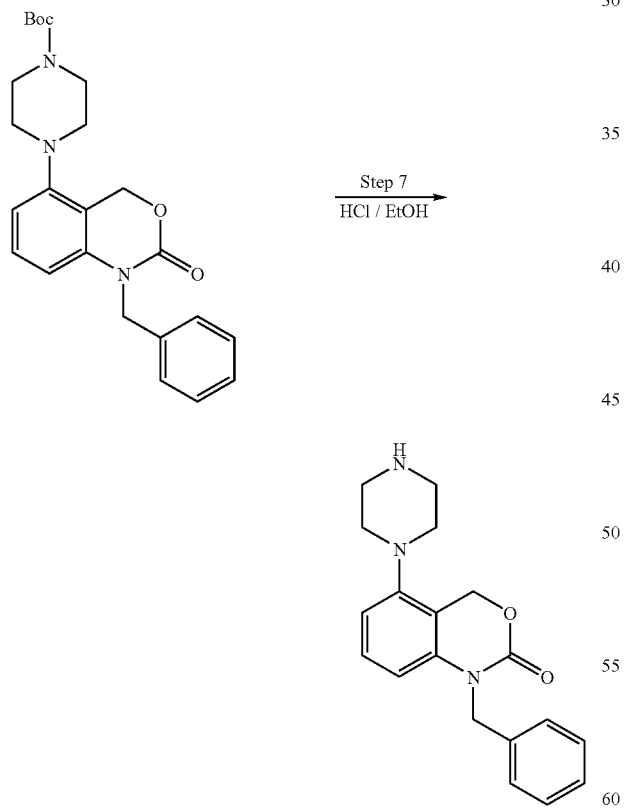

4-(1-Benzyl-2-oxo-1,4-dihydro-2H-benzo[d][1,3]oxazin-5-yl)-piperazine-1-carboxylic acid tert-butyl ester (33 mg, 0.08 mmol) was dissolved in 4 ml ethanol. To this solution was added 2 M ethanolic hydrochloric acid solution (1 ml). The reaction mixture was heated at 100° C. for 20 minutes, at which time a crystalline solid formed. The solution was allowed to cool to room temperature and 13 mg of 1-Benzyl-5-piperazin-1-yl-1,4-dihydro-benzo[d][1,3]oxazin-2-one hydrochloride salt was collected as a light yellow powder. MS: 324 (M+H)$^+$.

The following compounds were prepared in a similar fashion:

1-(2-Fluoro-benzyl)-5-piperazin-1-yl-1,4-dihydro-benzo[d][1,3]oxazin-2-one hydrochloride salt. MS: 342 (M+H)$^+$; and 1-(3-Fluoro-benzyl)-5-piperazin-1-yl-1,4-dihydro-benzo[d][1,3]oxazin-2-one hydrochloride salt. MS: 342 (M+H)$^+$.

Example 6

1-Benzyl-6-fluoro-5-piperazin-1-yl-3,4-dihydro-1H-quinazolin-2-one

The synthetic procedures described in this Example were carried out according to the process shown in Scheme I.

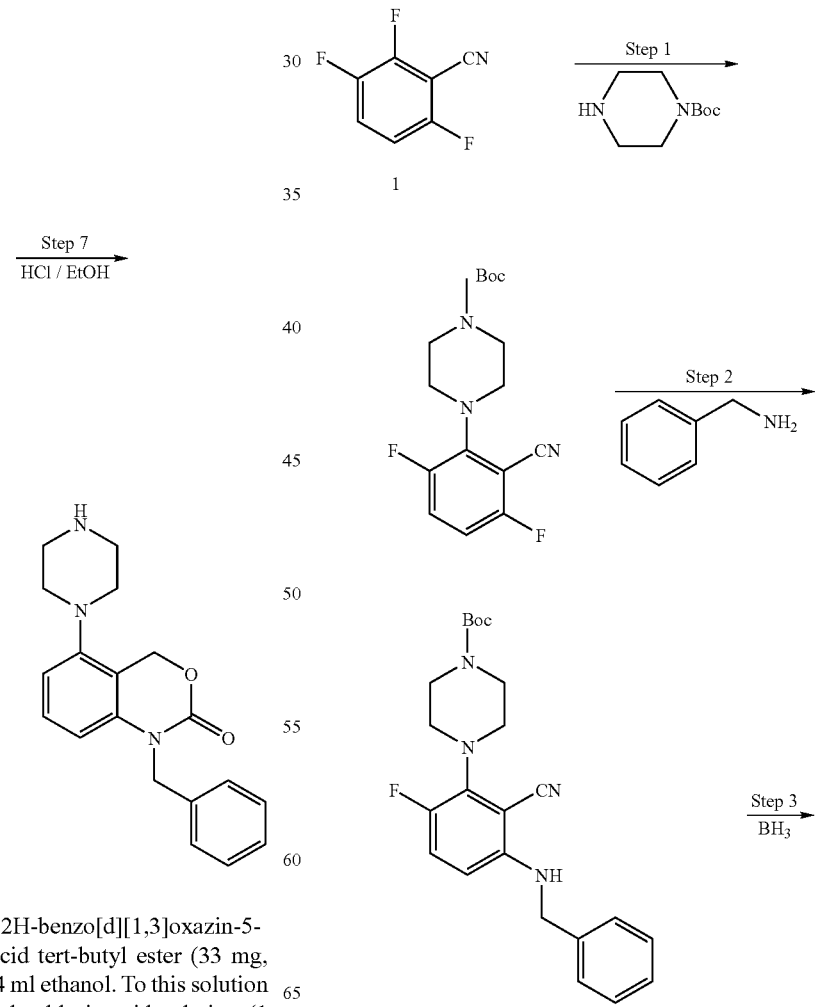

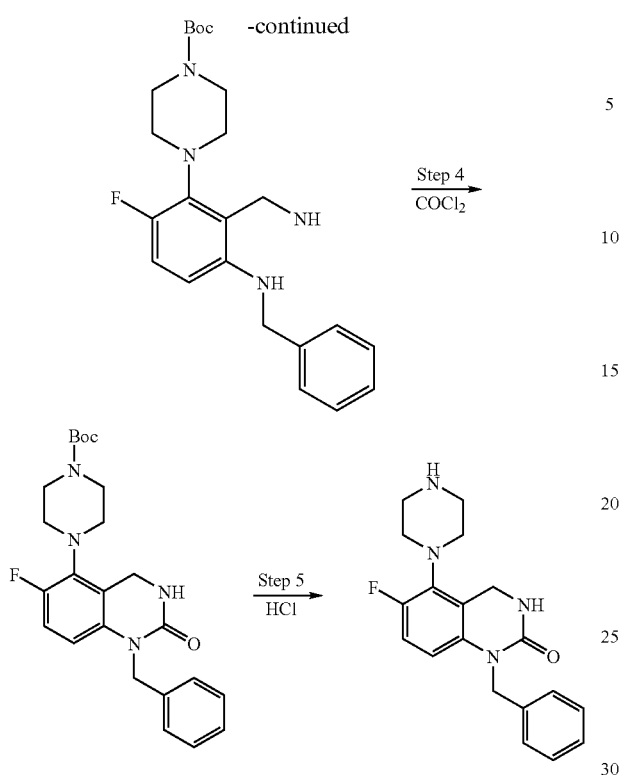

Step 4

4-(2-Cyano-3,6-difluoro-phenyl)-piperazine-1-carboxylic acid tert-butyl ester

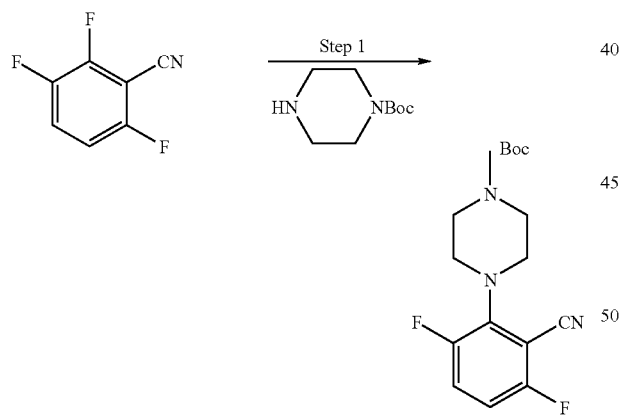

To 1.0 g (6.36 mmol) of 2,3,6-trifluorobenzonitrile dissolved in 10 mL DMF was added 1.05 g (1.2 eq., 7.63 mmol) potassium carbonate and 1.18 g (1 eq., 6.36 mmol) piperazine-1-carboxylic acid tert-butyl ester. The mixture was stirred 30 minutes to completion, partitioned between ethyl acetate and water, dried over magnesium sulfate and concentrated under reduced pressure. Column chromatography, eluting with ethyl acetate/hexanes provided 665 mg of 4-(2-cyano-3,6-difluoro-phenyl)-piperazine-1-carboxylic acid tert-butyl ester.

Step 2

4-(3-Benzylamino-2-cyano-6-fluoro-phenyl)-piperazine-1-carboxylic acid tert-butyl ester

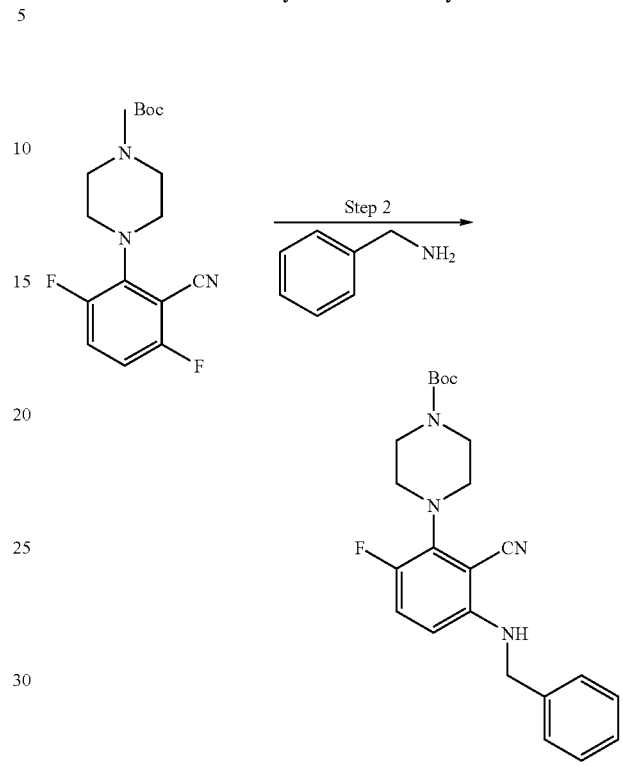

To 655 mg (2.03 mmol) of 4-(2-cyano-3,6-difluoro-phenyl)-piperazine-1-carboxylic acid tert-butyl ester dissolved in 10 mL DMF was added 560 mg (2 eq., 4.06 mmol) potassium carbonate and 243 µL (1.1 eq., 2.22 mmol) benzylamine. The mixture was heated to 100° C. for 5 days, cooled to room temperature and partitioned between ethyl acetate and water, dried over magnesium sulfate and concentrated. 4-(3-Benzylamino-2-cyano-6-fluoro-phenyl)-piperazine-1-carboxylic acid tert-butyl ester (288 mg) was precipitated from dichloromethane/hexanes.

Step 3

4-(2-Aminomethyl-3-benzylamino-6-fluoro-phenyl)-piperazine-1-carboxylic acid tert-butyl ester

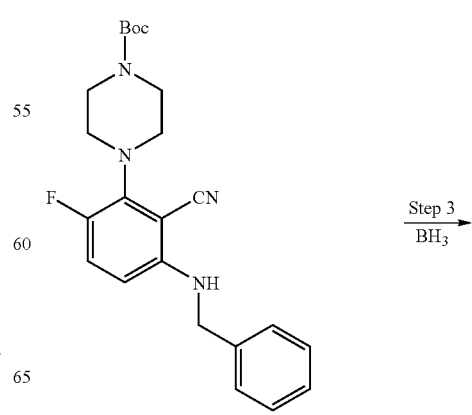

-continued

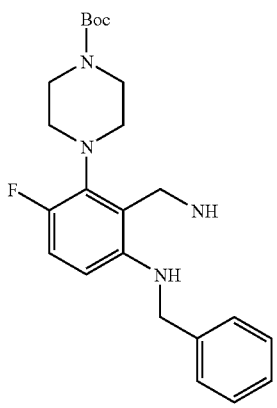

To 288 mg (0.7 mmol) of 4-(3-benzylamino-2-cyano-6-fluoro-phenyl)-piperazine-1-carboxylic acid tert-butyl ester dissolved in 7 mL tetrahydrofuran was added 1.4 mL (2 eq., 1.4 mmol, 1M in tetrahydrofuran)borane. The mixture was refluxed 10 hours and quenched with methanol, partitioned between ethyl acetate and water, dried over magnesium sulfate and concentrated to yield crude 4-(2-aminomethyl-3-benzylamino-6-fluoro-phenyl)-piperazine-1-carboxylic acid tert-butyl ester, which was used directly in the following step.

Step 4

4-(1-Benzyl-6-fluoro-2-oxo-1,2,3,4-tetrahydro-quinazolin-5-yl-piperazine-1-carboxylic acid tert-butyl ester

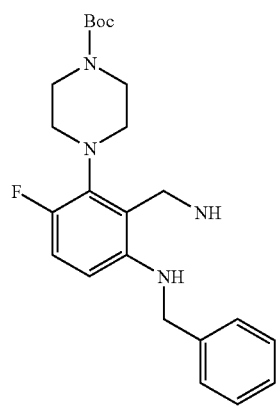

$\xrightarrow{\text{Step 4}}_{\text{COCl}_2}$

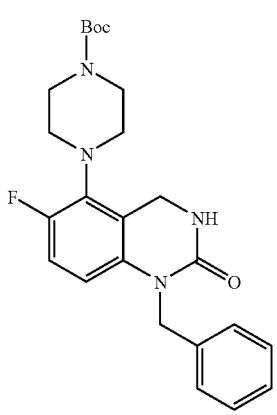

The crude 4-(2-aminomethyl-3-benzylamino-6-fluoro-phenyl)-piperazine-1-carboxylic acid tert-butyl ester of step 3 was dissolved in 10 mL dichloromethane and cooled to 0° C. Triethylamine (293 µL, 3 eq., 2.1 mmol) and 69 mg (1 eq., 0.233 mmol) triphosgene were added. The reaction mixture was stirred for 10 minutes. The mixture partitioned between ethyl acetate and water, dried over magnesium sulfate and concentrated. Column chromatography, eluting with acetone/dichlorometane provided 141 mg of 4-(1-benzyl-6-fluoro-2-oxo-1,2,3,4-tetrahydro-quinazolin-5-yl)-piperazine-1-carboxylic acid tert-butyl ester.

Step 5

1-Benzyl-6-fluoro-5-piperazin-1-yl-3,4-dihydro-1H-quinazolin-2-one

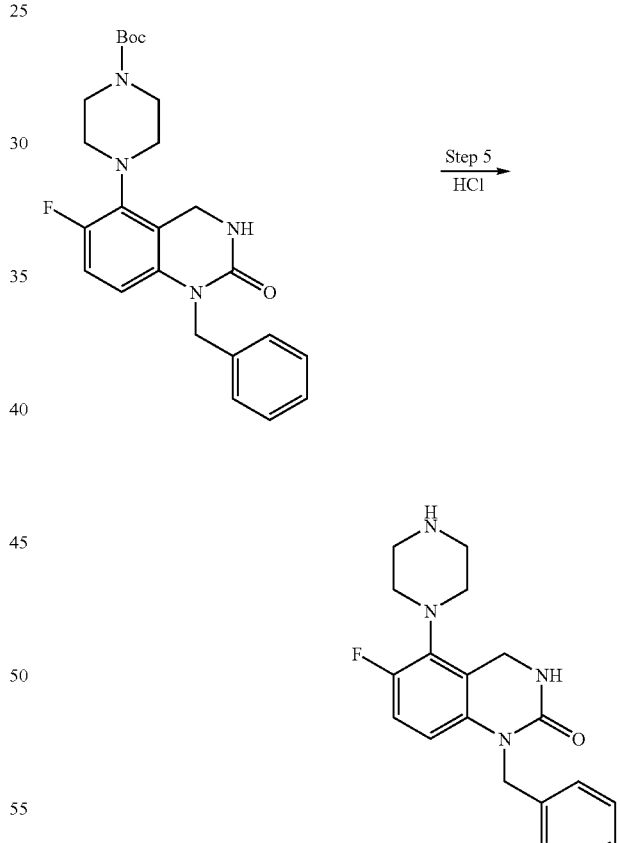

4-(1-Benzyl-6-fluoro-2-oxo-1,2,3,4-tetrahydro-quinazolin-5-yl)-piperazine-1-carboxylic acid tert-butyl ester (141 mg) was dissolved in 4 mL 2 N HCl/ethanol and heated to 80° C. for 20 minutes, then cooled to room temperature. Diethyl ether was added, precipitating 115 mg of 1-benzyl-6-fluoro-5-piperazin-1-yl-3,4-dihydro-1H-quinazolin-2-one hydrochloride. MP: 285.6–290.0° C. MS: 341 (M+H)$^+$.

Example 7
1-(3-Fluoro-benzyl)-7-methoxy-5-piperazin-1-yl-3,4-dihydro-1H-quinazolin-2-one
The synthetic procedures described in this Example were carried out according to the process shown in Scheme J.
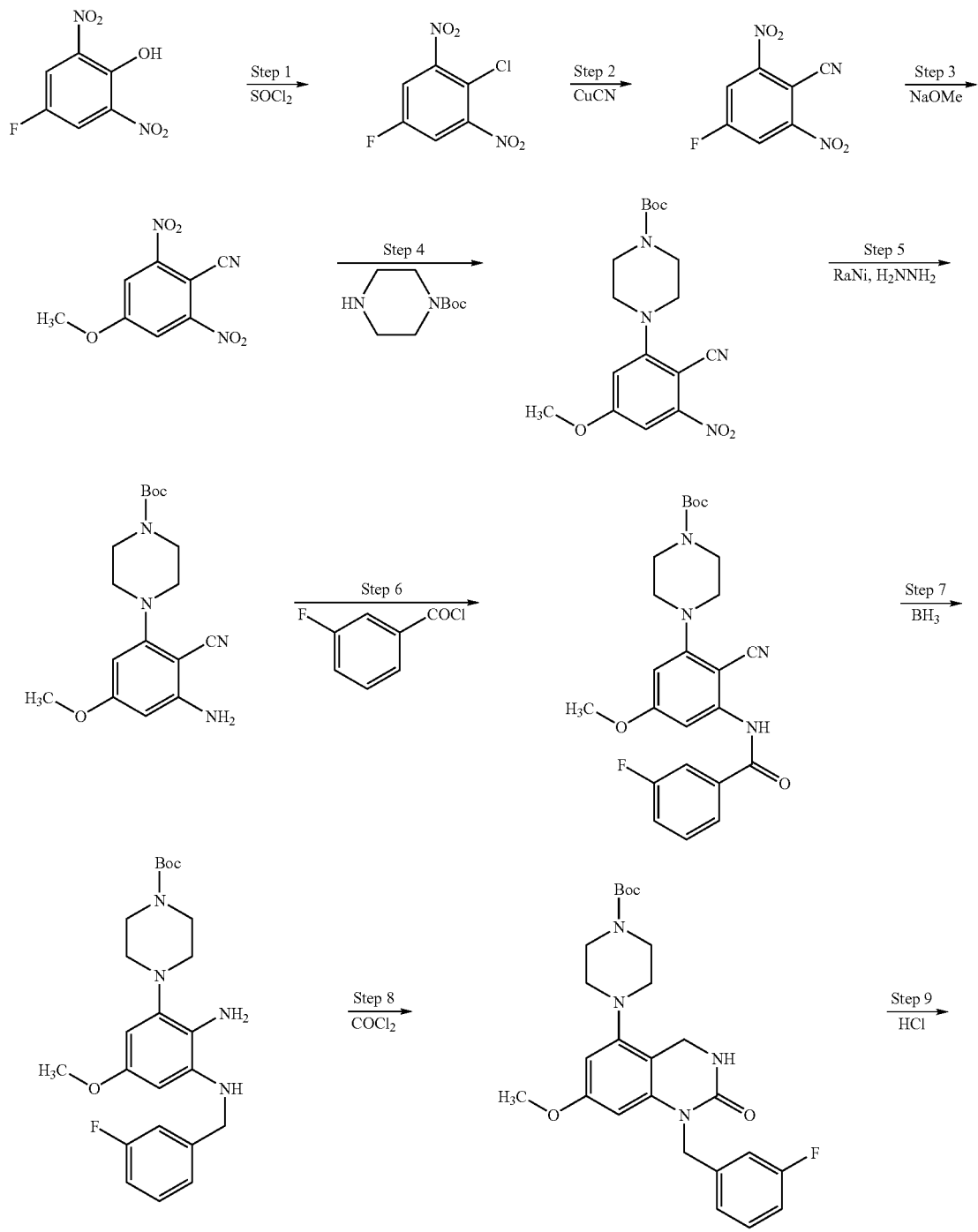
SCHEME J -continued

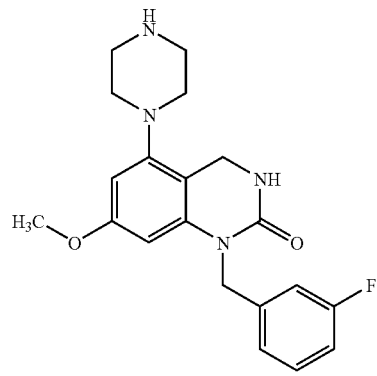

Step 1

2-Chloro-5-fluoro-1,3-dinitro-benzene

Step 3

4-Methoxy-2,6-dinitrobenzonitrile

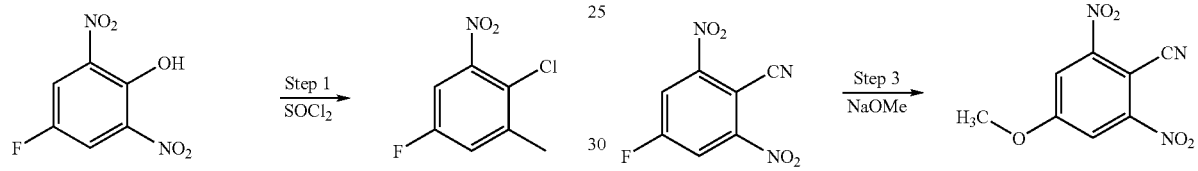

To 1.9 mL (24.74 mmol) of dimethyl formamide dissolved in 20 mL benzene was added 2.7 mL (37.11 mmol) thionyl chloride. The mixture was stirred for 10 minutes and 5.0 g (24.74 mmol) 4-fluoro-2,6-dinitrophenol was added. The mixture was refluxed 6 hours, cooled and concentrated under reduced pressure. The residue was recrystallized from ethanol to give 2-chloro-5-fluoro-1,3-dinitro-benzene (5.39 g).

To 1.92 g (9.11 mmol) of 4-fluoro-2,6-dinitrobenzonitrile dissolved in 20 mL methanol and 3 mL dimethylformamide at 0° C. was added 1.87 mL (1 eq., 4.87 M in methanol) sodium methoxide over 1 hour. The mixture was stirred an additional hour at 0° C., partitioned between ethyl acetate and water, dried over magnesium sulfate and concentrated under reduced pressure. Column chromatography, eluting with ethyl acetate/hexanes, provided 1.32 g of 4-methoxy-2,6-dinitrobenzonitrile.

Step 2

4-Fluoro-2,6-dinitrobenzonitrile

Step 4

4-(2-Cyano-5-methoxy-3-nitro-phenyl)-piperazine-1-carboxylic acid tert-butyl ester

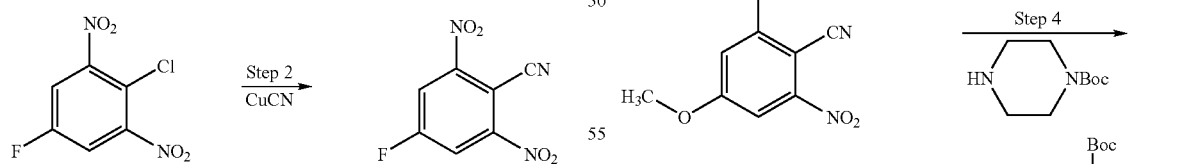

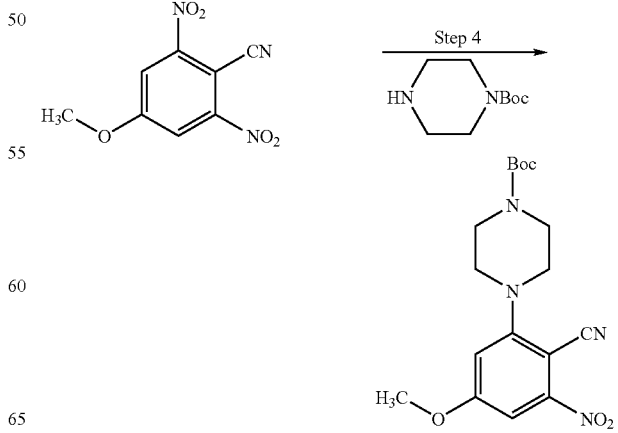

To 5.39 g (24.44 mmol) of 2-chloro-5-fluoro-1,3-dinitro-benzene dissolved in 20 mL dimethylformamide was added 2.63 g (1.2 eq., 29.27 mmol) copper cyanide. The mixture was stirred at 140° C. for 2 hours, cooled and partitioned between ethyl acetate and water, dried over magnesium sulfate and concentrated under reduced pressure. Column chromatography, eluting with ethyl acetate/hexanes, provided 1.44 g of 4-fluoro-2,6-dinitrobenzonitrile.

To 1.32 g (5.92 mmol) of 4-methoxy-2,6-dinitrobenzonitrile dissolved in 8 mL dimethylformamide was added 2.2 g (2 eq., 11.83 mmol) piperazine-1-carboxylic acid tert-butyl ester. The mixture was heated to 50° C. and stirred overnight, then partitioned between ethyl acetate and water, dried over magnesium sulfate and concentrated under reduced pressure. Column chromatography, eluting with ethyl acetate/hexanes provided 1.48 g of 4-(2-cyano-5-methoxy-3-nitro-phenyl)-piperazine-1-carboxylic acid tert-butyl ester.

Step 5

4-(3-Amino-2-cyano-5-methoxy-phenyl)-piperazine-1-carboxylic acid tert-butyl ester

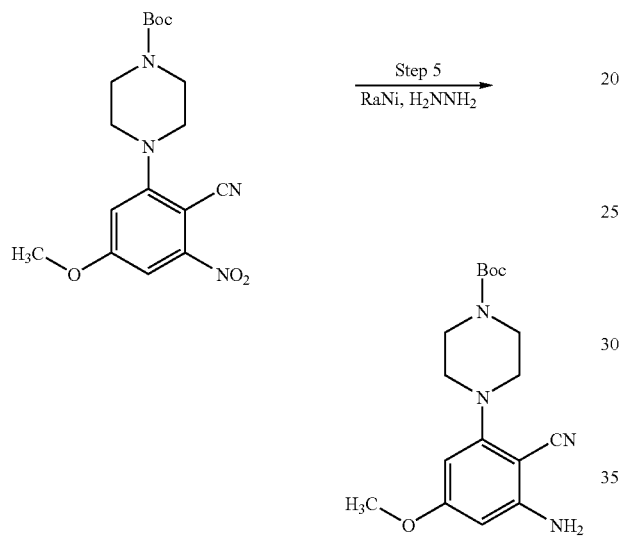

To 370 mg (1.02 mmol) of 4-(2-cyano-5-methoxy-3-nitro-phenyl)-piperazine-1-carboxylic acid tert-butyl ester dissolved in 5 mL ethanol and 5 mL ethyl acetate was added a pipet of Raney nickel slurry in water followed by 64 μL (2 eq., 2.04 mmol) hydrazine. The mixture was stirred 30 minutes to completion, filtered through Celite and concentrated under reduced pressure to provide 300 mg of crude 4-(3-amino-2-cyano-5-methoxy-phenyl)-piperazine-1-carboxylic acid tert-butyl ester.

Step 6

4-(3-Benzoylamino-2-cyano-5-methoxy-phenyl)-piperazine-1-carboxylic acid tert-butyl ester

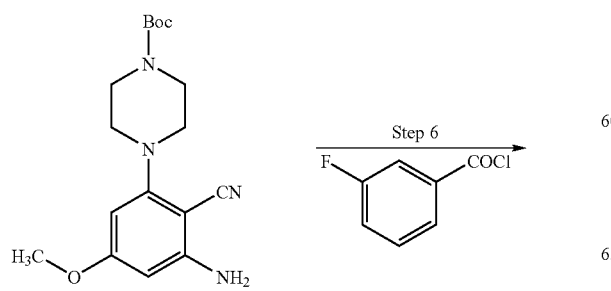

-continued

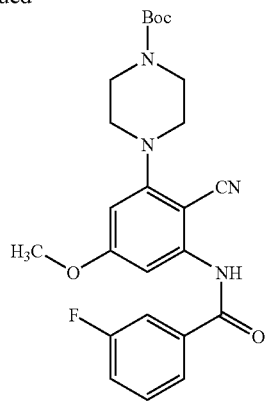

To 300 mg (0.856 mmol) of crude product 11 dissolved in 10 mL dichloromethane was added 138 μL (2 eq., 1.71 mmol) pyridine followed by 104 μL (1 eq., 0.856 mmol) 3-fluorobenzoyl chloride. The mixture was stirred 1 hour, partitioned between ethyl acetate and water, dried over magnesium sulfate and concentrated. Column chromatography, eluting with ethyl acetate/hexanes provided 186 mg of 4-(3-benzoylamino-2-cyano-5-methoxy-phenyl)-piperazine-1-carboxylic acid tert-butyl ester.

Step 7

4-(2-Aminomethyl-3-benzylamino-5-methoxy-phenyl)-piperazine-1-carboxylic acid tert-butyl ester

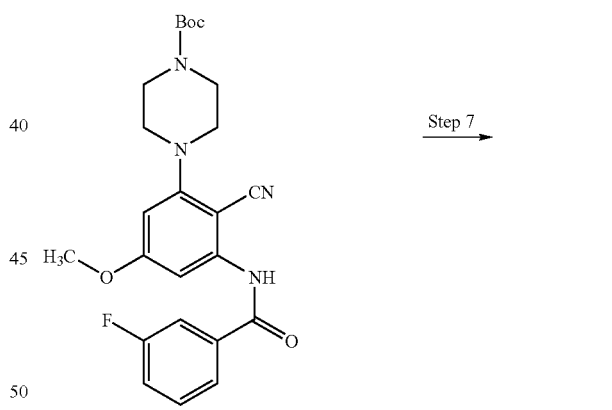

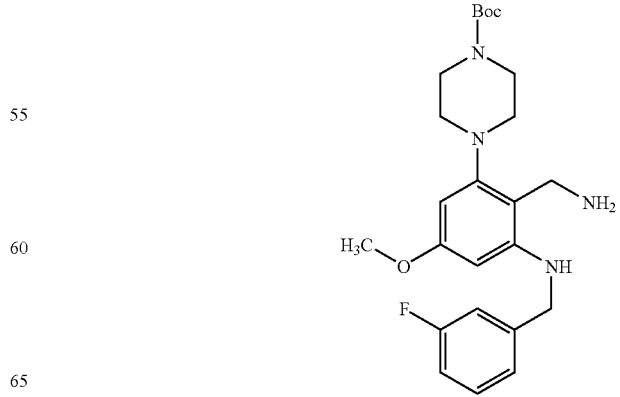

To 186 mg (0.39 mmol) of 4-(3-benzoylamino-2-cyano-5-methoxy-phenyl)-piperazine-1-carboxylic acid tert-butyl ester dissolved in 10 mL tetrahydrofuran was added 1.57 mM (4 eq., 1.57 mmol) borane (1M in tetrahydrofuran). The mixture was heated to reflux overnight, cooled and quenched with methanol, partitioned between ethyl acetate and water, dried over magnesium sulfate and concentrated under reduced pressure to provide 153 mg of crude 4-(2-aminomethyl-3-benzylamino-5-methoxy-phenyl)-piperazine-1-carboxylic acid tert-butyl ester.

Step 8

4-[1-(3-Fluoro-benzyl)-7-methoxy-2-oxo-1,2,3,4-tetrahydro-quinazolin-5-yl]-piperazine-1-carboxylic acid tert-butyl ester

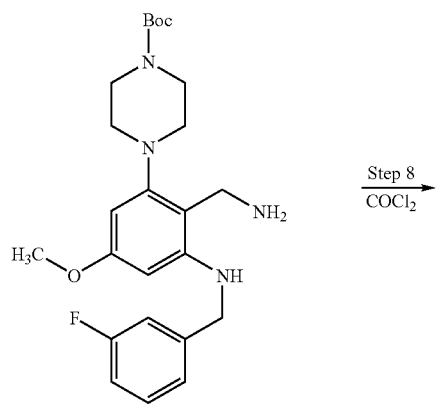

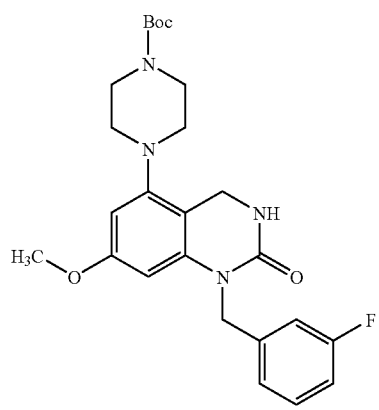

4-(2-Aminomethyl-3-benzylamino-5-methoxy-phenyl)-piperazine-1-carboxylic acid tert-butyl ester (153 mg) was dissolved in 6 mL dichloromethane and cooled to 0° C. Triethylamine (138 μL, 3 eq., 0.99 mmol) and 33 mg (1 eq., 0.11 mmol) triphosgene were added. The reaction was stirred for 30 minutes. The mixture was partitioned between ethyl acetate and water, dried over magnesium sulfate and concentrated under reduced pressure. Column chromatography, eluting with ethyl acetae/hexanes provided 43 mg of 4-[1-(3-fluoro-benzyl)-7-methoxy-2-oxo-1,2,3,4-tetrahydro-quinazolin-5-yl]-piperazine-1-carboxylic acid tert-butyl ester.

Step 9

1-(3-Fluoro-benzyl)-7-methoxy-5-piperazin-1-yl-3,4-dihydro-1H-quinazolin-2-one

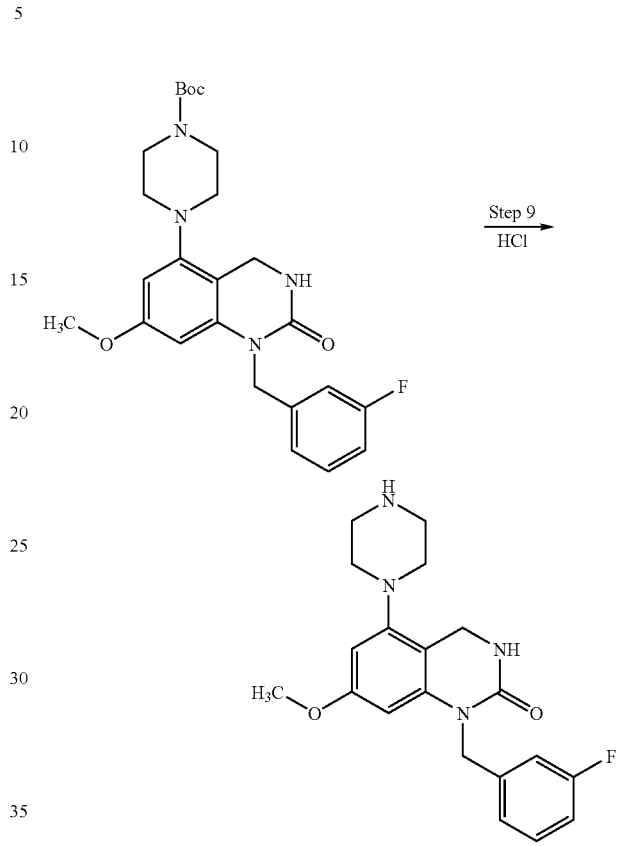

4-[1-(3-Fluoro-benzyl)-7-methoxy-2-oxo-1,2,3,4-tetrahydro-quinazolin-5-yl]-piperazine-1-carboxylic acid tert-butyl ester (43 mg) was dissolved in 4 mL 2N HCl/ethanol and heated to 80° C. for 20 minutes. The reaction mixture was cooled to room temperature, and ether was added, precipitating 18 mg of 1-(3-fluoro-benzyl)-7-methoxy-5-piperazin-1-yl-3,4-dihydro-1H-quinazolin-2-one. MS: 371 (M+H)$^+$.

Example 8

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an

| Composition for Oral Administration | |
| --- | --- |
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
| --- | --- |
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
| --- | --- |
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 9

Radioligand Binding Studies

This example illustrates in vitro radioligand binding studies of compound of formula I.

The binding activity of compounds of this invention in vitro was determined as follows. Duplicate determinations of $5-HT_6$ ligand affinity were made by competing for binding of [$^3$H]LSD in cell membranes derived from HEK293 cells stably expressing recombinant human $5-HT_6$ receptor. Duplicate determinations of $5-HT_{2A}$ ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO-K1 cells stably expressing recombinant human $5-HT_2A$ receptor. Membranes were prepared from HEK 293 cell lines by the method described by Monsma et al., Molecular Pharmacology, Vol. 43 pp. 320–327 (1993), and from CHO-K1 cell lines as described by Bonhaus et al., Br J. Pharmacol. June; 115(4): 622–8 (1995).

For estimation of affinity at the $5-HT_6$ receptor, all determinations were made in assay buffer containing 50 mM Tris-HCl, 10 mM $MgSO_4$, 0.5 mM EDTA, 1 mM ascorbic acid, pH 7.4 at 37° C., in a 250 microliter reaction volume. For estimation of affinity at the $5-HT_{2A}$ receptor all determinations were made in assay buffer containing 50 mM Tris-HCl, 5 mM ascorbic acid, 4 mM CaCl2, pH 7.4 at 32° C., in a 250 microliter reaction volume.

Assay tubes containing [³H] LSD or [³H]Ketanserin (5 nM), competing ligand, and membrane were incubated in a shaking water bath for 75 min. at 37° C. (for 5-HT$_6$) or 60 min. at 32° C. (for 5-HT$_{2A}$), filtered onto Packard GF-B plates (pre-soaked with 0.3% PEI) using a Packard 96 well cell harvester and washed 3 times in ice cold 50 mM Tris-HCl. Bound [³H] LSD or [³H]Ketanserin were determined as radioactive counts per minute using Packard TopCount.

Displacement of [³H]LSD or [³H]Ketanserin from the binding sites was quantified by fitting concentration-binding data to a 4-parameter logistic equation:

$$\text{binding} = \text{basal} + \left( \frac{Bmax - \text{basal}}{1 + 10^{-Hill(\log[ligand] - \log IC_{50})}} \right)$$

where Hill is the Hill slope, [ligand] is the concentration of competing radioligand and IC$_{50}$ is the concentration of radioligand producing half-maximal specific binding of radioligand. The specific binding window is the difference between the Bmax and the basal parameters.

Using the procedures of this Example, compounds of Formula I were tested and found to be 5-HT6 and/or 5-HT2A antagonists. For example, the compound 1-(2,3-difluoro-benzyl)-7-ethyl-5-piperazin-1-yl-3,4-dihydro-1H-quinazolin-2-one exhibited a phi of approximately 9.89 for the 5-HT6 receptor, and 1-(3-chloro-benzyl)-5-piperazin-1-yl-7-trifluoromethyl-3,4-dihydro-1H-quinazolin-2-one exhibited a pKi of approximately 8.89 for the 5-HT2A receptor.

Example 10

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47–59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of the formula (I):

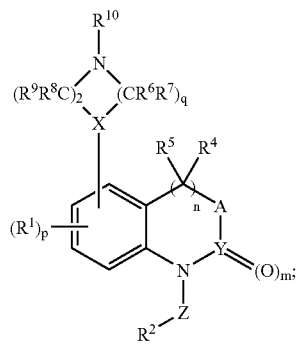

or a pharmaceutically acceptable salt or prodrug thereof, wherein;

Y is C;

m is 1;

n is 1;

p is from 0 to 3;

q is from 1 to 3;

Z is —(C$R^a R^b$)$_r$— or —SO$_2$—, where r is from 0 to 2 and each of $R^a$ and $R^b$ is independently hydrogen or alkyl;

X is CH or N;

each $R^1$ is independently halo, alkyl, haloalkyl, heteroalkyl, alkoxy, cyano, —S(O)$_s$—$R^c$, —C(=O)—N$R^c R^d$, —SO$_2$—N$R^c R^d$, —N($R^c$)—C(=O)—$R^d$, or —C(=O) $R^c$, where s is from 0 to 2 and each of $R^c$ and $R^d$ is independently hydrogen or alkyl;

$R^2$ is optionally substituted aryl or optionally substituted heteroaryl;

A is —N$R^3$— wherein $R^3$ is hydrogen, alkyl, acyl, amidoalkyl, hydroxyalkyl or alkoxyalkyl;

each of $R^4$ and $R^5$ is independently hydrogen or alkyl, or $R^4$ and $R^5$ together with their shared carbon may form a carbocyclic ring of 3 to 6 members; and each of $R^6$, $R^7$, $R^8$, $R^9$ and $R^{10}$ is independently hydrogen or alkyl, or one of $R^6$ and $R^7$ together wit $R^{10}$ and the atoms to which they are attached may form a heterocyclic ring of 3 to 7 members, or one of $R^6$ and $R^7$ together with one of $R^8$ and $R^9$ and the atoms to which they are attached may form a heterocyclic ring of 3 to 7 members.

2. The compound of claim 1, wherein Z is —(C$R^a R^b$)$_r$—.
3. The compound of claim 2, wherein X is N and q is 2.
4. The compound of claim 3, wherein r is 1.
5. The compound of claim 4, wherein $R^a$ and $R^b$ are hydrogen.
6. The compound of claim 5, wherein $R^2$ is optionally substituted phenyl or optionally substituted naphthyl.
7. The compound of claim 6, wherein $R^4$ and $R^5$ are hydrogen.
8. The compound of claim 1, wherein said compound is of the formula (II)

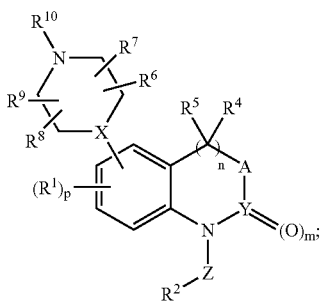

and wherein X, Y, Z, A, $R^1$, $R^2$, $R^4$, $R^5$, $R^6$, $R^7$, $R^8$, $R^9$, $R^{10}$, m, n, and p are as recited in claim 1.

9. The compound of claim 1, wherein said compound is of the formula (III):

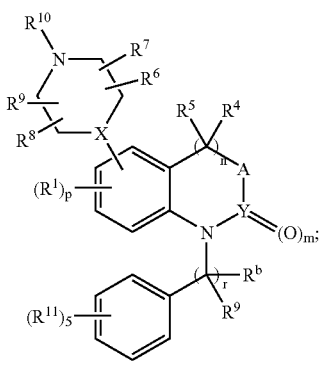

and wherein:
s is from 0 to 4;
each $R^{11}$ independently is alkyl, alkoxy, halo, cyano or haloalkyl; and
X, Y, A, $R^1$, $R^2$, $R^4$, $R^5$, $R^6$, $R^7$, $R^8$, $^9$, $R^{10}$, $R^a$, $R^b$, m, n, p and r are as recited in claim 1.

10. The compound of claim 9, wherein said compound is of the formula (IV):

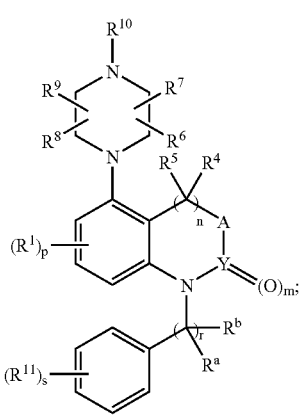

and wherein Y, A, $R^1$, $R^2$, $R^4$, $R^5$, $R^6$, $R^7$, $R^8$, $R^9$, $R^{10}$, $R^{11}$, $R^a$, $R^b$, m, n, p, r and s are as recited in claim 9.

11. The compound of claim 10, wherein r is 1 and $R^a$ and $R^b$ are hydrogen.

12. The compound of claim 11, wherein n is 1 and $R^4$ and $R^5$ are hydrogen.

13. The compound of claim 10, wherein said compound is of the formula (V):

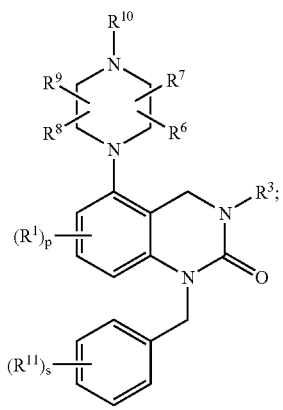

and wherein $R^1$, $R^2$, $R^3$, $R^6$, $R^7$, $R^8$, $R^9$, $R^{10}$, $R^{11}$, p and s are as recited in claim 10.

14. A pharmaceutical composition comprising an effective amount of the compound of claim 1 in admixture with a pharmaceutically acceptable carrier.

15. The compound of claim 6, wherein $R^2$ is phenyl, 2-halophenyl, 3-halophenyl, 4-halophenyl, 2-cyanophenyl, 3-cyanophenyl, 4-cyanophenyl, 2-methoxyphenyl, 3-methoxyphenyl, 4-methoxyphenyl, 2,3-dihalophenyl, 2,4-dihalophenyl, 2,5-dihalophenyl, 2,6-dihalophenyl, 3,4-dihalophenyl, 3,5 -dihalophenyl, 2-methylphenyl, 3-methylphenyl, or 2,2-dimethyl-2,3-dihydro-benzofuranyl, wherein each said halo is independently fluoro or chloro.

16. The compound of claim 6, wherein p is 0 or 1 and $R^1$ is halo, alkyl, haloalkyl, or alkoxy.

17. The compound of claim 6, wherein $R^6$, $R^7$, $R^8$ and $R^9$ are hydrogen.

18. The compound of claim 17, wherein $R^3$ is hydrogen.

19. The compound of claim 1, wherein said compound is selected from the group consisting of:
1-Benzyl-5-piperazin-1-yl-3,4-dihydro-1H-quinazolin-2-one;
1-Benzyl-3-methyl-5-piperazin-1-yl-3,4-dihydro-1H-quinazolin-2-one;
1-(3-Fluoro-benzyl)-5-piperazin-1-yl-3,4-dihydro-1H-quinazolin-2-one;
1-(4-Fluoro-benzyl)-5-piperazin-1-yl-3,4-dihydro-1H-quinazolin-2-one;
1-(2-Fluoro-benzyl)-5-piperazin-1-yl-3,4-dihydro-1H-quinazolin-2-one;
1-(4-Chloro-benzyl)-5-piperazin-1-yl-3,4-dihydro-1H-quinazolin-2-one;
1-(2-Chloro-benzyl)-5-piperazin-1-yl-3,4-dihydro-1H-quinazolin-2-one;
1-(3-Chloro-benzyl)-5-piperazin-1-yl-3,4-dihydro-1H-quinazolin-2-one;
1-(3,4-Difluoro-benzyl)-5-piperazin-1-yl-3,4-dihydro-1H-quinazolin-2-one;
1-(3,4-Dichloro-benzyl)-5-piperazin-1-yl-3,4-dihydro-1H-quinazolin-2-one;

1-(2,3-Difluoro-benzyl)-5-piperazin-1-yl-3,4-dihydro-1H-quinazolin-2-one;
1-(2,3-Dichloro-benzyl)-5-piperazin-1-yl-3,4-dihydro-1H-quinazolin-2-one;
1-(3-Chloro-2-fluoro-benzyl)-5-piperazin-1-yl-3,4-dihydro-1H-quinazolin-2-one;
1-(2-Fluoro-benzyl)-3-methyl-5-piperazin-1-yl-3,4-dihydro-1H-quinazolin-2-one;
1-(3-Fluoro-benzyl)-3-methyl-5-piperazin-1-yl-3,4-dihydro-1H-quinazolin-2-one;
1-(4-Fluoro-benzyl)-3-methyl-5-piperazin-1-yl-3,4-dihydro-1H-quinazolin-2-one;
3-(3-Methyl-2-oxo-5-piperazin-1-yl-3,4-dihydro-2H-quinazolin-1-ylmethyl)-benzonitrile;
3-Ethyl-1-(4-fluoro-benzyl)-5-piperazin-1-yl-3,4-dihydro-1H-quinazolin-2-one;
2-(1-Benzyl-2-oxo-5-piperazin-1-yl-1,4-dihydro-2H-quinazolin-3-yl)-acetamide;
1-Benzyl-3-ethyl-5-piperazin-1-yl-3,4-dihydro-1H-quinazolin-2-one;
2-[1-(3-Fluoro-benzyl)-2-oxo-5-piperazin-1-yl-1,4-dihydro-2H-quinazolin-3-yl]-acetamide;
1-(3-Fluoro-benzyl)-5-piperazin-1-yl-3,4-dihydro-1H-quinazolin-2-one;
1-Benzyl-3-isopropyl-5-piperazin-1-yl-3,4-dihydro-1H-quinazolin-2-one;
1-(2-Fluoro-benzyl)-3-isopropyl-5-piperazin-1-yl-3,4-dihydro-1H-quinazolin-2-one;
1-(3-Chloro-benzyl)-3-isopropyl-5-piperazin-1-yl-3,4-dihydro-1H-quinazolin-2-one;
1-(2,3-Difluoro-benzyl)-3-isopropyl-5-piperazin-1-yl-3,4-dihydro-1H-quinazolin-2-one;
1-(2-Methyl-benzyl)-5-piperazin-1-yl-3,4-dihydro-1H-quinazolin-2-one;
1-(4-Fluoro-benzyl)-3-isopropyl-5-piperazin-1-yl-3,4-dihydro-1H-quinazolin-2-one;
1-(3-Fluoro-benzyl)-3-isopropyl-5-piperazin-1-yl-3,4-dihydro-1H-quinazolin-2-one;
1-(2-Methyl-benzyl)-5-piperazin-1-yl-3,4-dihydro-1H-quinazolin-2-one;
1-(2-Chloro-benzyl)-7-methyl-5-piperazin-1-yl-3,4-dihydro-1H-quinazolin-2-one;
1-(2-Fluoro-benzyl)-7-methyl-5-piperazin-1-yl-3,4-dihydro-1H-quinazolin-2-one;
1-(2,3-Dimethyl-benzyl)-5-piperazin-1-yl-3,4-dihydro-1H-quinazolin-2-one;
1-(2,2-Dimethyl-2,3-dihydro-benzofuran-7-ylmethyl)-5-piperazin-1-yl-3,4-dihydro-1H-quinazolin-2-one;
1-(2,6-Dimethyl-benzyl)-5-piperazin-1-yl-3,4-dihydro-1H-quinazolin-2-one;
1-Benzyl-5-piperazin-1-yl-7-trifluoromethyl-3,4-dihydro-1H-quinazolin-2-one;
1-(3-Fluoro-benzyl)-7-methyl-5-piperazin-1-yl-3,4-dihydro-1H-quinazolin-2-one;
1-Benzyl-7-ethyl-5-piperazin-1-yl-3,4-dihydro-1H-quinazolin-2-one;
7-Ethyl-1-(3-fluoro-benzyl)-5-piperazin-1-yl-3,4-dihydro-1H-quinazolin-2-one;
7-Ethyl-1-(2-fluoro-benzyl)-5-piperazin-1-yl-3,4-dihydro-1H-quinazolin-2-one;
1-(2-Chloro-benzyl)-7-ethyl-5-piperazin-1-yl-3,4-dihydro-1H-quinazolin-2-one;
1-(3-Fluoro-benzyl)-7-methoxy-5-piperazin-1-yl-3,4-dihydro-1H-quinazolin-2-one;
1-(2,6-Difluoro-benzyl)-5-piperazin-1-yl-3,4-dihydro-1H-quinazolin-2-one;
1-(2-Fluoro-benzyl)-5-piperazin-1-yl-7-trifluoromethyl-3,4-dihydro-1H-quinazolin-2-one;
1-(3-Fluoro-benzyl)-5-piperazin-1-yl-7-trifluoromethyl-3,4-dihydro-1H-quinazolin-2-one;
1-Benzyl-6-fluoro-5-piperazin-1-yl-3,4-dihydro-1H-quinazolin-2-one;
1-(3-Chloro-benzyl)-7-ethyl-5-piperazin-1-yl-3,4-dihydro-1H-quinazolin-2-one;
1-(2,3-Difluoro-benzyl)-7-ethyl-5-piperazin-1-yl-3,4-dihydro-1H-quinazolin-2-one;
1-(2-Fluoro-benzyl)-7-methyl-5-(4-methyl-piperazin-1-yl)-3,4-dihydro-1H-quinazolin-2-one;
1-(3-Fluoro-benzyl)-5-(4-methyl-piperazin-1-yl)-3,4-dihydro-1H-quinazolin-2-one;
1-(2,6-Difluoro-benzyl)-7-ethyl-5-piperazin-1-yl-3,4-dihydro-1H-quinazolin-2-one;
7-Ethyl-5-piperazin-1-yl-1-(2-trifluoromethyl-benzyl)-3,4-dihydro-1H-quinazolin-2-one; and
1-(3-Chloro-benzyl)-5-piperazin-1-yl-7-trifluoromethyl-3,4-dihydro-1H-quinazolin-2-one.

* * * * *